US012639472B2

(12) United States Patent
Davydov et al.

(10) Patent No.: US 12,639,472 B2
(45) Date of Patent: May 26, 2026

(54) SYSTEM AND METHOD OF INTEGRATED UNIQUE IDENTITY MANAGEMENT

(71) Applicant: Spinal Guides Labs, LLC, Carolina, PR (US)

(72) Inventors: Albert Davydov, Carolina, PR (US); Peter Usov, Belle Mead, NJ (US)

(73) Assignee: Spinal Guides Labs, LLC, Carolina, PR (US)

( * ) Notice: Subject to any disclaimer, the term of this patent is extended or adjusted under 35 U.S.C. 154(b) by 58 days.

(21) Appl. No.: 18/901,840

(22) Filed: Sep. 30, 2024

(65) Prior Publication Data

US 2025/0021691 A1      Jan. 16, 2025

Related U.S. Application Data

(63) Continuation-in-part of application No. 16/890,477, filed on Jun. 2, 2020, now abandoned, which is a continuation-in-part of application No. 16/879,176, filed on May 20, 2020, now abandoned, which is a continuation-in-part of application No. 16/383,698, filed on Apr. 15, 2019, now abandoned.

(60) Provisional application No. 63/586,822, filed on Sep. 29, 2023.

(51) Int. Cl.
| | |
|---|---|
| *G06F 21/62* | (2013.01) |
| *G06F 21/32* | (2013.01) |
| *G06Q 20/02* | (2012.01) |
| *G06Q 20/38* | (2012.01) |
| *G06Q 20/40* | (2012.01) |
| *G06V 40/16* | (2022.01) |
| *G16H 10/60* | (2018.01) |

(52) U.S. Cl.
CPC .......... *G06F 21/6245* (2013.01); *G06F 21/32* (2013.01); *G06Q 20/02* (2013.01); *G06Q 20/3829* (2013.01); *G06Q 20/40145* (2013.01); *G06V 40/171* (2022.01); *G16H 10/60* (2018.01); *G06Q 2220/00* (2013.01)

(58) Field of Classification Search
CPC ..... G06F 21/6245; G06F 21/32; G16H 10/60; G06V 40/171; G06Q 20/02; G06Q 20/3829; G06Q 20/40145
See application file for complete search history.

(56) References Cited

U.S. PATENT DOCUMENTS

| | | | |
|---|---|---|---|
| 6,859,780 B1 | 2/2005 | Cunningham | |
| 7,519,591 B2 | 4/2009 | Landi et al. | |
| 9,465,858 B2 | 10/2016 | Pennefather et al. | |
| 11,251,959 B2 | 2/2022 | Wentz | |
| 2003/0140928 A1* | 7/2003 | Bui ........................ | G16H 10/60 |
| | | | 128/898 |
| 2005/0209886 A1 | 9/2005 | Corkern | |

(Continued)

OTHER PUBLICATIONS

Lauren Riplinger et al., Patient Identification Techniques—Approaches, Implications, and Findings, IMIA Yearbook of Medical Informatics. (Year: 2020).*

*Primary Examiner* — Shanto Abedin

(74) *Attorney, Agent, or Firm* — Michael J Porco

(57) ABSTRACT

The system and method of integrated unique identity management by generating a unique person identifier using the person's personal information combined with person's biometric data. The unique person identifier serves as a special patient tag with universal abilities allowing for the person's identity to be managed across various data sources.

13 Claims, 10 Drawing Sheets

(56)     References Cited

U.S. PATENT DOCUMENTS

| | | | |
|---|---|---|---|
| 2006/0293925 A1* | 12/2006 | Flom ...................... | G07C 9/257 |
| | | | 707/999.009 |
| 2007/0002894 A1 | 1/2007 | Peterson | |
| 2007/0047770 A1 | 3/2007 | Swope et al. | |
| 2010/0119126 A1* | 5/2010 | Rane ...................... | G06V 10/28 |
| | | | 382/125 |
| 2010/0299158 A1 | 11/2010 | Siegel | |
| 2012/0051370 A1 | 3/2012 | Thevenon et al. | |
| 2012/0205453 A1* | 8/2012 | Rampersad ............ | G06Q 50/26 |
| | | | 235/487 |
| 2012/0271733 A1 | 10/2012 | Brooks | |
| 2013/0251214 A1 | 9/2013 | Chung | |
| 2018/0374100 A1 | 12/2018 | Zhou et al. | |
| 2019/0205887 A1 | 7/2019 | Kimmel | |
| 2020/0327558 A1 | 10/2020 | Davydov et al. | |
| 2020/0327965 A1* | 10/2020 | Davydov ................ | G06F 16/22 |
| 2020/0327968 A1 | 10/2020 | Davydov et al. | |

* cited by examiner

| Reference # | Item |
|---|---|
| 1 | User/patient |
| 2 | Biometric Scanner Activation |
| 3 | Type in Biometric Data for PIT Generation |
| 4 | PIT is created |
| 5 | PBD is created |
| 6 | UPIE is created |
| 7 | Local database of local medical facility |
| 8 | Request with PIT |
| 9 | Global UPI from PGIS |
| 10 | Global UPI |
| 11 | Request with PBD out of plurality of PITs |
| 12 | Receive Global UPI and Copying it into the Local UPI |
| 13 | When PTI=0, request with PBD and PIT as UPIE is sent |
| 14 | UPIE is saved as UPI in PGIS |
| 15 | Connections to HIES |
| 16 | Request to EHR |
| 17 | Electronic health record (EHR) Providers |
| 18 | Patient identity manager |
| 19 | Local Medical Facility Healthcare Software App |
| 20 | Response from EHR |
| 70 | Local medical facility |
| 72 | PGIS Global Server |

LEGEND

FIG. 2B

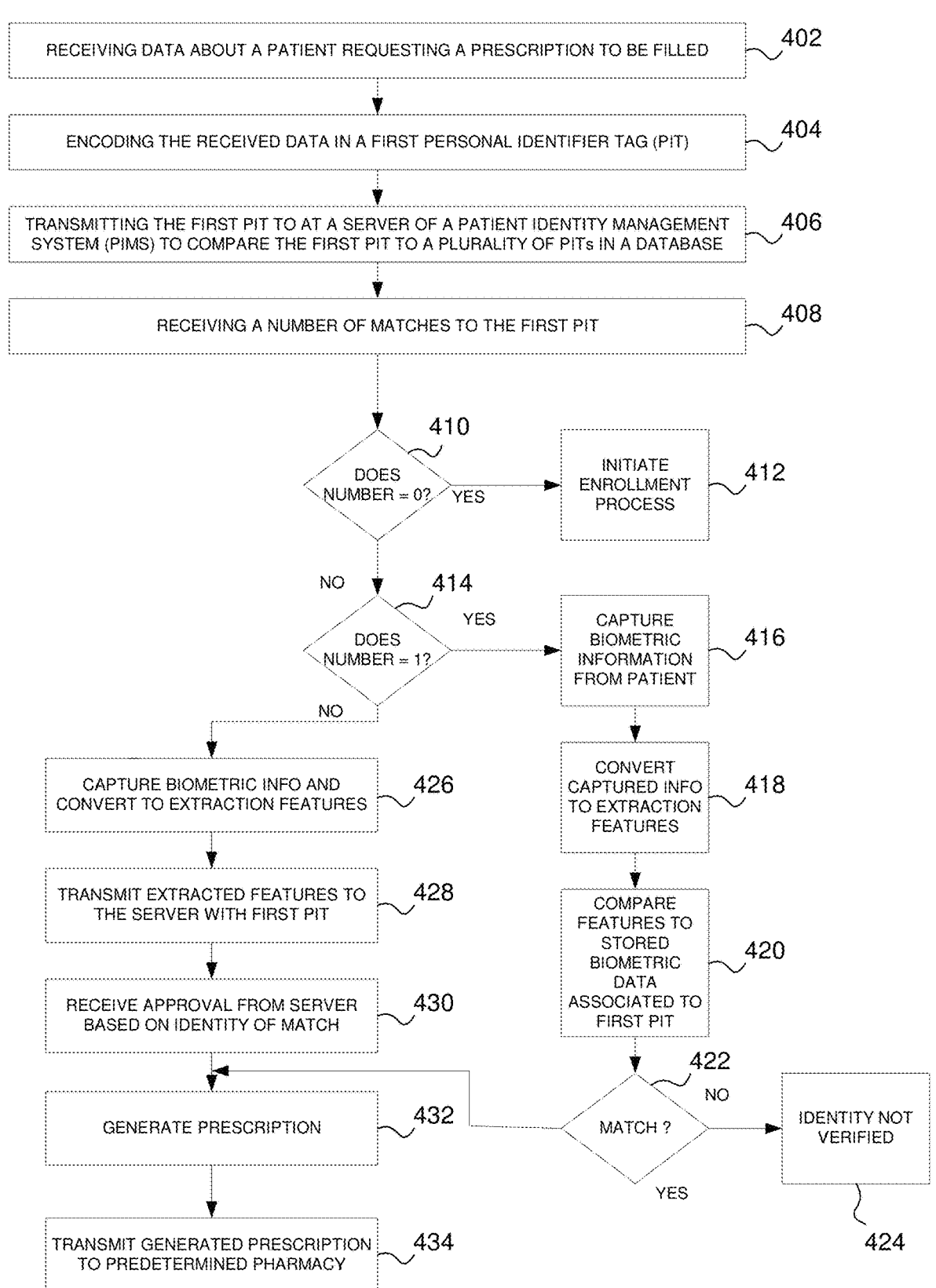

402 — RECEIVING DATA ABOUT A PATIENT REQUESTING A PRESCRIPTION TO BE FILLED

404 — ENCODING THE RECEIVED DATA IN A FIRST PERSONAL IDENTIFIER TAG (PIT)

406 — TRANSMITTING THE FIRST PIT TO AT A SERVER OF A PATIENT IDENTITY MANAGEMENT SYSTEM (PIMS) TO COMPARE THE FIRST PIT TO A PLURALITY OF PITs IN A DATABASE

408 — RECEIVING A NUMBER OF MATCHES TO THE FIRST PIT

410 — DOES NUMBER = 0?

412 — INITIATE ENROLLMENT PROCESS

414 — DOES NUMBER = 1?

416 — CAPTURE BIOMETRIC INFORMATION FROM PATIENT

426 — CAPTURE BIOMETRIC INFO AND CONVERT TO EXTRACTION FEATURES

418 — CONVERT CAPTURED INFO TO EXTRACTION FEATURES

428 — TRANSMIT EXTRACTED FEATURES TO THE SERVER WITH FIRST PIT

420 — COMPARE FEATURES TO STORED BIOMETRIC DATA ASSOCIATED TO FIRST PIT

430 — RECEIVE APPROVAL FROM SERVER BASED ON IDENTITY OF MATCH

422 — MATCH ?

432 — GENERATE PRESCRIPTION

424 — IDENTITY NOT VERIFIED

434 — TRANSMIT GENERATED PRESCRIPTION TO PREDETERMINED PHARMACY

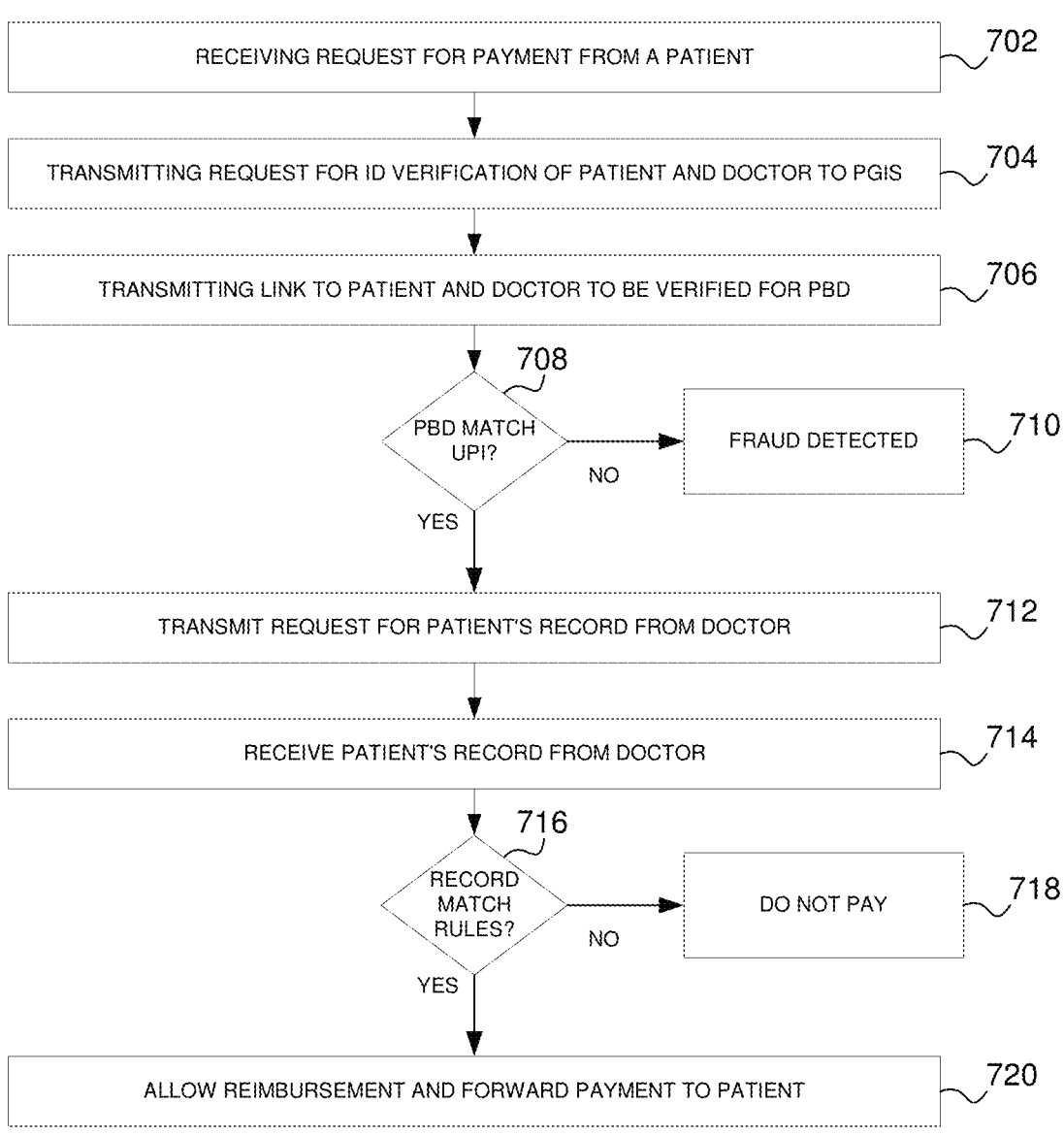

RECEIVING REQUEST FOR PAYMENT FROM A PATIENT — 702

TRANSMITTING REQUEST FOR ID VERIFICATION OF PATIENT AND DOCTOR TO PGIS — 704

TRANSMITTING LINK TO PATIENT AND DOCTOR TO BE VERIFIED FOR PBD — 706

708

PBD MATCH UPI? — NO → FRAUD DETECTED — 710

YES

TRANSMIT REQUEST FOR PATIENT'S RECORD FROM DOCTOR — 712

RECEIVE PATIENT'S RECORD FROM DOCTOR — 714

716

RECORD MATCH RULES? — NO → DO NOT PAY — 718

YES

ALLOW REIMBURSEMENT AND FORWARD PAYMENT TO PATIENT — 720

FIG. 7

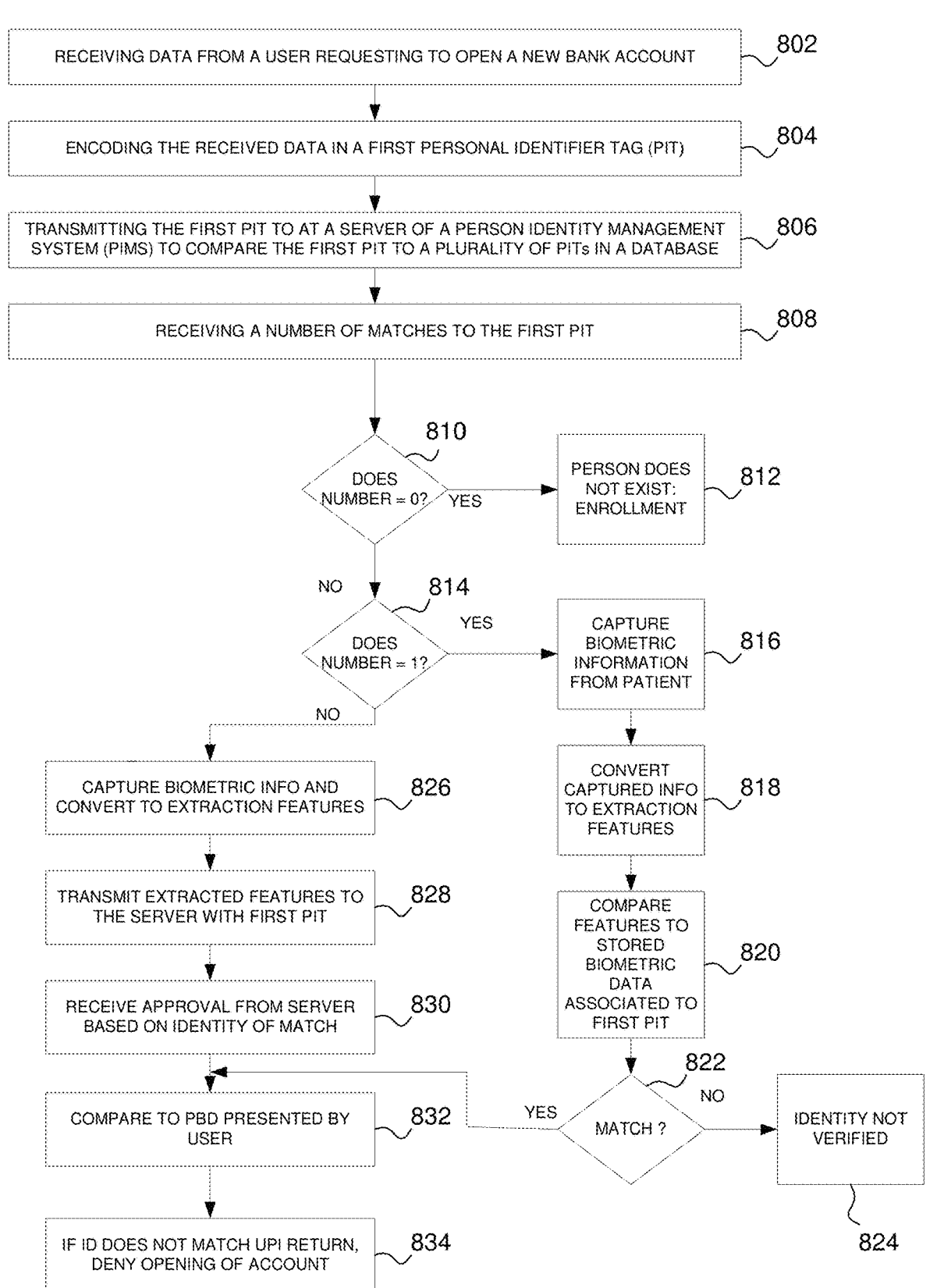

RECEIVING DATA FROM A USER REQUESTING TO OPEN A NEW BANK ACCOUNT — 802

ENCODING THE RECEIVED DATA IN A FIRST PERSONAL IDENTIFIER TAG (PIT) — 804

TRANSMITTING THE FIRST PIT TO AT A SERVER OF A PERSON IDENTITY MANAGEMENT SYSTEM (PIMS) TO COMPARE THE FIRST PIT TO A PLURALITY OF PITs IN A DATABASE — 806

RECEIVING A NUMBER OF MATCHES TO THE FIRST PIT — 808

810 — DOES NUMBER = 0?

YES → PERSON DOES NOT EXIST: ENROLLMENT — 812

NO

814 — DOES NUMBER = 1?

YES → CAPTURE BIOMETRIC INFORMATION FROM PATIENT — 816

NO

CAPTURE BIOMETRIC INFO AND CONVERT TO EXTRACTION FEATURES — 826

CONVERT CAPTURED INFO TO EXTRACTION FEATURES — 818

TRANSMIT EXTRACTED FEATURES TO THE SERVER WITH FIRST PIT — 828

COMPARE FEATURES TO STORED BIOMETRIC DATA ASSOCIATED TO FIRST PIT — 820

RECEIVE APPROVAL FROM SERVER BASED ON IDENTITY OF MATCH — 830

COMPARE TO PBD PRESENTED BY USER — 832

822 — MATCH ?

NO → IDENTITY NOT VERIFIED — 824

YES

IF ID DOES NOT MATCH UPI RETURN, DENY OPENING OF ACCOUNT — 834

FIG. 8

SYSTEM AND METHOD OF INTEGRATED UNIQUE IDENTITY MANAGEMENT

PRIORITY

This application claims priority to U.S. Provisional Patent Application No. 63/586,822, filed Sep. 29, 2023, entitled "SYSTEM AND METHOD OF INTEGRATED UNIQUE IDENTITY MANAGEMENT", the contents of which are hereby incorporated by reference in its entirety.

The present application is also a continuation-in-part application claiming priority to pending U.S. patent application Ser. No. 16/890,477 for METHOD OF PREVENTING PHARMACEUTICAL FRAUD USING INTEGRATED IDENTITY MANAGEMENT, filed on Jun. 2, 2020, which is a continuation-in-part application of pending U.S. patent application Ser. No. 16/879,176 for SYSTEM AND METHOD OF INTEGRATED PATIENT UNIQUE IDENTITY MANAGEMENT, filed on May 20, 2020, which is a continuation-in-part claiming priority to U.S. patent application Ser. No. 16/383,698 for SYSTEM AND METHOD OF INTEGRATED PATIENT UNIQUE IDENTITY MANAGEMENT, filed on Apr. 15, 2019, now abandoned.

BACKGROUND

Field The present invention is in the field of systems and methods for identifying personal data. More specifically, the present invention is an integrated personal data unique identity management system and a method to identify each person within a global computer system.

The present invention is a system and a method of integrated personal data unique identity management based on human biometric data and a special personal tag with universal abilities of managing person's identity across data sources.

Additionally, the present invention is a system and method of using the unique identification to prevent unauthorized distribution of controlled substances through legal channels through pharmacies.

Background The following background information may present examples of specific aspects of the prior art (e.g., without limitation, approaches, facts, or common wisdom) that, while expected to be helpful to further educate the reader as to additional aspects of the prior art, it is not to be construed as limiting the present invention, or any embodiments thereof, to anything stated or implied therein, or inferred thereupon.

Electronic equipment typically may fail at some point during the lifetime of a device. Often the cause of failure may be resolved with specific procedures and/or actions. Certain electronic equipment may come equipped with user displays that may inform a user on the nature of a failure and/or provide steps to resolve a failure. There may be cases where a user may not have the necessary expertise, permissions, and/or knowledge to resolve a failure and may require additional support. A typical solution may include a user calling a device manufacturer's tech support and requesting aid. A user may also search a database, technical manuals, and/or the internet for failure resolutions. Generally, traditional solutions may require a user to dedicate a non-trivial amount of time to resolve a failure.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that some electronic devices may capture problem or problem data that is displayed to a user and forwarded to a manufacturer for failure support. Some electronic devices may also come equipped with imaging apparatuses that allow a user to take an image of an electronic device for failure detection and/or resolution.

Personal data in many industries, and electronic health care data in healthcare, in particular, are always tried to be linked together across multiple systems, including electronic health records (EHRs), patient registries, claims databases. In general, each system assigns its own identifier to each person whose data it maintains. This process makes it difficult to track data across multiple systems and identify duplicate data entry when different systems are linked. Efforts to address this challenge are complicated by the need to protect data privacy and security.

Personal Data Global Unique Identification System (PDGUIS) is defined as the system with abilities to ascertain a distinct, unique identity as expressed by an identifier that is unique within the scope of the exchange network, given characteristics about that identity such as name, date of birth and gender. PDGUIS utilizes the process to accurately and appropriately identify, track, manage, link individuals and their digitized health or other information, often within and across multiple electronic systems.

A related idea is the concept of personal identity integrity defined as the accuracy and completeness of data attached to, or associated with an individual. Efficient identity management leads to high identity integrity. One of the solutions is to assign a personal identifier tag (PIT), to each person's unique body part patterns (some human body part patterns can be subject for unique identification) and share it among data storage facilities. There are biometric data collection devices utilized based on this attribute for security identification and authentication purposes. However, each individual device system contains certain percentage of inaccuracy and has capability issues.

For example, fingerprint method, the oldest and the most popular biometric technology is only 99.3 percent reliable. Fingerprint databases of U.S. government agencies alone store more than 200 million records. However, quality issues respective to degrading prints, or development of skin calluses over time during hard and repetitive labor complicate the read. More effective, in terms of accuracy were the palm vein biometric devices. However, they are also problematic due to high pattern template size and high cost. Other methods and devices may seriously limit the possibilities of their applications in global and nationwide identity systems.

In addition, a simple generation of global unique identification numbers requires a centralized generation system and a distribution system for these numbers. There are also problems of assigning the unique numbers to individuals. There are also problems arising from assigning different numbers to the same individual, or for different individuals' assignment the same number. In such cases, these numbers cannot be used as incidental because they are not synchronized. For example, medical institutions erroneously assign duplicate numbers to one person. Or, in a personal identity fraud personal identification can be stolen and an identifier (ID) can be assigned to someone else.

Using above methods simultaneously create the person's (or in healthcare, patient's) global unique identification system. It combines biometric data to verify a person's (patient's) identity and assigns the unique individual number to make the system more accurate and flexible. This approach eliminates most problems described above because the biometrics can prevent individuals from registering in the global unique identification system multiple times and, vice versa, an individual unique number of a person can be retrieved from the global system using biometric data.

Unfortunately, this method also has serious limitations for globalization. Biometric patterns, or templates, must be stored on a central server during enrollment. Direct matching process of biometric patterns or templates may take a long time. A personal biometric template captured by the biometric device must be sent to the central server that requires good network, internet connectivity and sufficient hardware operating resources.

Accuracy in this process depends on several other factors such as false acceptance rate (FAR), false reject rate (FRR), error rate, identification rate, etc. Significant disadvantage of those limitations is the fact that the system cannot operate with institutions that have no internet connection or internet connection is unstable. In this case, it would be advantageous to have a system that can generate a unique person's IDs from personal identification locally without any connection to the central database. Such a system will be more reliable and easier to use in the PDGUIS.

The unique ID can be formed based on individual data of a person such as first, middle and last names, birthday in combination with personal unique body part pattern, or template.

On the other hand, personal unique body part pattern, or template can be supplied with an individual person's, or as in healthcare, Patient Individual Tag (PIT), based on individual data of a person.

This approach reduces the personal IDs data fetch duration from the national database and increase accuracy in storing data. However, limitations for wide application of this system can be lack of accuracy of the processing and measurements issues and a high cost of instruments.

Today, common biometric approaches include facial recognition, fingerprinting and iris scanning. These systems are limited due to their complexity, infringement on privacy, cost, or portability issues.

SUMMARY

The present invention of the method and system offers a simple, cost-effective and portable solution with high accuracy, fast search speed for biometric patterns, or templates in the global database storage.

The present invention describes using ear biometrics and it is not limited to it. Any biometrics can be used as well. Ear biometrics has proven to be a unique and viable solution. It does not require particular actions, such as scanning of a part of a body over an authentication device which makes it easier to conduct continuous authentication. The system works everywhere, even when the person is moving. Ears are remarkably consistent unlike faces, they do not change shape with different expressions, or age and remain fixed in the middle of the side of the head against a predictable background.

In the present invention, we have developed an identification algorithm that also shows good scalability of recognition rate with size of a dataset. We then conducted re-recognition and then identification and statistical analyses to identify the accuracy and replicability of our method. In conclusion, the bend, or flexure of the ear helix was found to be the most reliable anatomical structure that could be served as the base for re-identification.

It is known that single ear identification rate might vary from 90% to 99.5% for image ray transform methods. In the present invention, our approach is to use both, left and right ears together and our rate of identification was up to 100%.

The present invention is a simple, cost-effective and portable personal identification method in the global system that allows managing identity across countrywide data sources. It minimizes data management expenses such as storage requirements for the device itself. The personal data will be stored locally. There is only a simple web camera and a simple image processing application, or a lightweight image processing application necessary.

The present invention can be used in many industries. The examples could be healthcare global ID verification for medical equipment, electronic healthcare (EHR) patient record management and management of patient identity across data sources. The national patient identification system would identify patients, link patient medical records, and allow broad sharing, monitoring, research and analysis of public using computerized medical records linked through the Nationwide Health Information Network (NHIN). Other examples may include government organizations, national identity applications, financial institutions and other facilities requiring high security storage. Personal data information exchange enables information sharing across disparate health care applications. It also can be used as a platform for development of biometric identification application for desktop and mobile devices. System can meet the minimum hardware requirements for current mobile devices on the market today and can be used on many mobile devices such as Android, or the Apple IOS system, or a like.

According to one aspect of the present disclosure, a computer-implemented method for retrieving a record of a patient includes processing, by at least one processor, a set of personal data of a person to generate a specific integer number formed from said set of personal data by first converting a first type of personal data, wherein the first type of personal data comprises alphanumeric and non-alphanumeric characters, into a converted personal data string by removing all non-alphanumeric characters; next converting the converted personal data string to a second personal data string wherein all alphanumeric characters are in uppercase, then converting the second personal data string to a number string with at least four parts, wherein a first part is a number value which is calculated as the sum of ASCII values of first letters of each word in the converted personal data string, wherein a second part of said number string comprises values representing a selected day, wherein a third part of said number string is calculated from a length value of the words in the converted personal data string plus a coefficient number, wherein a fourth part of said number string is based on a physical characteristic of said person, and wherein said number string formed independently of a global computing system is used to identify said person; processing, by the at least one processor, a set of biometric data formed independently of the global computing system obtained by scanning at least a portion of a body of said person with a biometric imaging device to obtain an image and then processing the image using at least one imaging algorithm to extract features of the portion of the body of said person; combining, by the at least one processor, said generated number string with the extracted features of the portion of the body of said person to generate a unique person's identifier independently of the global computing system; storing a plurality of unique person's identifiers in a database, each unique person's identifier having a respective generated number string and respective generated extracted features; in response to a request for retrieval of at least one data record of a particular person, verifying, by the at least one processor, an identity of the particular person by comparing a received number string of said particular person to the number strings of the plurality of unique person's identifiers in the database and, if more than one match occurs, comparing said person's extracted features to the extracted features of the plurality of the matches of the unique person's identifiers to verify the identity of the particular person; and retrieving, by the at least one processor, at least one data record associated to the particular person upon verifying the identity of the particular person.

In one aspect, the portion of the body of said person is at least one ear of said person and the at least one imaging algorithm is an image ray transform function, wherein the image ray transform function locates and extracts at least one region of the ear.

In another aspect, a portion of the first type of personal data is the full name of a person and a first name of a mother of said person.

In a further aspect, the selected day is a birthday in a form of a combination of a day number, a month number, and a year number of the birthday.

In one aspect, a portion of the first type of personal data is a number representing an eye color of said person.

In another aspect, the at least one processor further processes an image of at least one of said person's palm vein, fingerprint, iris and face.

In yet another aspect, the at least one algorithm further converts the extracted regions of the ear into extracted features using linear time-invariant filter responses.

In one aspect of the present disclosure, a method for generating a pharmaceutical prescription includes receiving, by a first server, general data about a patient requesting to have a prescription filled; encoding, by the first server, the general data into a first Personal Identifier Tag (PIT); transmitting, by the first server via a communications network, the first PIT to a Patient Identity Management System (PIMS) computing device including a database to allow the PIMS computing device to electronically compare the first PIT with a plurality of other PIT entries in the database representing a plurality of other patients and to allow the PIMS computing device to determine if one or more entries in the database correspond with the first PIT; upon receiving, at the first server via the communications network, a notification from the PIMS computing device that one or more entries correspond with the first PIT, capturing physically an image of the patient via at least one biometric capture device coupled to the first server, converting the image into at least one extraction feature and combining the PIT with the at least one extraction feature to generate a Unique Patient Identification Entity (UPIE); transmitting, by the first server via the communications network, prescription request information along with the UPIE to a computing device of a controlling entity to allow the computing device of the controlling entity to identify the patient by searching the database with the PIT and the at least one extraction feature and determine if the prescription request meets applicable medical rules for the identified patient; and upon receiving, via the communications network, an approval response from the computing device of the controlling entity indicating that the prescription request meets the applicable medical rules for the identified patient based on the UPIE of the patient, automatically transmitting, by the first server via the communications network, the prescription to be filled for the patient to at least one computing device of a predetermined pharmacy with a copy of the approval response from the controlling entity.

In another aspect, the general data includes at least a name of the patient, a name of a mother of the patient and birthday of the patient.

In a further aspect, the step of encoding the general data includes one or more algorithms for manipulating one or more of the ASCII values of multiple characters in the patient's name, patient's mother name, the length of the patient's name, and numbers representing the year, month, and day of the patient's birthday.

In yet another aspect, the general data further includes biometric information obtainable in a non-intrusive manner.

In still another aspect, the biometric information includes at least the eye color of the patient.

In one aspect, the step of physically capturing an image of the patient includes capturing one or more images of one or both ears of the patient; and the step of converting the image into at least one extraction feature includes extracting curvature information from the one or more images to detect anatomical characteristics of one or both of the patient's ears.

In yet another aspect, the step of extracting the curvature information includes an image ray transform algorithm.

In one aspect, the method further includes the step of: upon receiving, via the communications network, a rejection response from the controlling entity indicating that the prescription request does not meet the applicable medical rules for the identified patient, providing an alert of possible pharmaceutical fraud.

In another aspect of the present disclosure, a method for negotiating a check includes receiving, by a first financial institution server, a check to be negotiated, the check including an encrypted barcode, the encrypted barcode including a unique personal identifier (UPI) of a user of a second financial institution, the UPI generated by a $3^{rd}$ party server and includes a personal identifier tag (PIT) and personal biometric data (PBD) of the user of the second financial institution; transmitting, by the first financial institution server, the check to a second financial institution server; requesting the second financial institution server for payment associated to the check to the first financial institution server, the request including the check; decrypting, by the second financial institution server, the barcode on the check with a decryption key, the decryption key provided by the $3^{rd}$ party server; identifying, by the second financial institution server, the user of the second financial institution using the decrypt barcode and retrieving contact information of the user; transmitting, by the second financial institution server, an approval request to a device of the user based on the retrieved contact information; receiving, at the second financial institution server, the approval from the device of the user; and upon receiving the approval of the second financial institution of the user, transmitting, by the second financial institution server, the funds to the first financial institution server.

In another aspect, the method further includes generating the approval by the device of the second financial institution user, wherein the generating the approval includes obtaining the personal biometric data (PBD) of the second financial institution user by the device of the second financial institution user.

In a further aspect, the personal biometric data (PBD) of the second financial institution user includes at least two different biometric items of the user.

In yet another aspect, the at least two biometric items include at least one of extracted features of an ear, a fingerprint, iris scan, facial image and/or a video stream of a face.

In one aspect, the device of the second financial institution user is a mobile device, the mobile device including an image capture device.

In still a further aspect, the approval request is at least one of a text, phone call and/or email.

In a further aspect of the present disclosure, a method for opening a bank account includes receiving, by a first server, general data about a user requesting to open a new bank account; encoding, by the first server, the general data into a first Personal Identifier Tag (PIT); transmitting, by the first server via a communications network, the first PIT to a Person Identity Management System (PIMS) computing device including a database to allow the PIMS computing device to electronically compare the first PIT with a plurality of other PIT entries in the database representing a plurality of other persons and to allow the PIMS computing device to determine if one or more entries in the database correspond with the first PIT; upon receiving, at the first server via the communications network, a notification from the PIMS computing device that one or more entries correspond with the first PIT, capturing physically an image of the user via at least one biometric capture device coupled to the first server, converting the image into at least one extraction feature and combining the PIT with the at least one extraction feature to generate a Unique Person Identification Entity (UPIE); transmitting, by the first server via the communications network, the UPIE to the PIMS computing device to identify the user by searching the database with the PIT and the at least one extraction feature and determine the identity of the user; and upon receiving, via the communications network, an approval response from the PIMS computing device opening the new bank account, and upon receiving a denial response, reporting an indication of attempted fraud.

In yet another aspect of the present disclosure, a method for processing an insurance claim includes receiving, via a computing device, a request for payment from a patient; transmitting, via the computing device, a request for identity verification of the patient and a doctor associated to the patient; transmitting, via the computing device, a link to the patient and doctor to verify respective personal biometric data; comparing the respective personal biometric data with a respective unique personal identifier (UPI) associated to the patient and doctor; upon receiving a confirmation of matches, transmitting a request for at least one record of the patient from the doctor; and upon receiving the at least one record of the patient, automatically, forwarding the requested payment to the patient.

In a further aspect of the present disclosure, a system for generating a unique person identification entity (UPIE) formed locally, independent from the global server, i.e., the PGIS server, includes at least one processor that receives a set of personal data of a person and generates a personal identification tag (PIT) formed from said set of personal data by first converting a first type of personal data, wherein the first type of personal data comprises alphanumeric and non-alphanumeric characters, into a converted personal data string by removing all non-alphanumeric characters; next converting the converted personal data string to a second personal data string wherein all alphanumeric characters are in uppercase, then converting the second personal data string to a number string with at least four parts, wherein a first part is a number value which is calculated as the sum of ASCII values of first letters of each word in the converted personal data string and on a physical characteristic of said person, wherein a second part of said number string comprises values representing a selected day, wherein a third part of said number string is calculated from a length value of the words in the converted personal data string plus a coefficient number; and a biometric scanning device coupled to the at least one processor, the biometric scanning device configured to capture a set of biometric data by scanning at least a portion of a body of said person to obtain an image and transmitting the obtained image to the at least one processor; the at least one processor processes the obtained image using at least one imaging algorithm to extract features of the portion of the body of said person to create personal biometric data (PBD); and the at least one processor combines the PIT with PBD to generate a unique person identification entity (UPIE).

In one aspect, the at least one processor stores a plurality of UPIEs in a database, each UPIE having a respective generated PIT and respective generated PBD.

In another aspect, the portion of the body of said person is at least one ear of said person and the at least one imaging algorithm is an image ray transform function, wherein the image ray transform function locates and extracts at least one region of the ear.

In a further aspect, a portion of the first type of personal data is the full name of a person and a first name of a mother of said person.

In yet another aspect, the selected day is a birthday in a form of a combination of a day number, a month number, and a year number of the birthday.

In one aspect, a portion of the first type of personal data is a number representing an eye color of said person.

In still another aspect, the at least one processor further processes an image of at least one of said person's palm vein, fingerprint, iris and face.

In another aspect, the at least one algorithm further converts the extracted regions of the ear into extracted features using linear time-invariant filter responses.

BRIEF DESCRIPTION OF THE DRAWINGS

The present invention will be described by way of exemplary embodiments, but not limitations, illustrated in the accompanying drawings in which like references denote similar elements, and in which:

FIG. 2B is a legend for FIG. 2A in accordance with an embodiment of the present disclosure.

FIG. 4 illustrates a method for preventing fraudulent obtainment of controlled substances with the use of fake ID from pharmacies in accordance with an embodiment of the present disclosure.

FIG. 6 illustrates an exemplary record of an individual in accordance with an embodiment of the present disclosure.

FIG. 7 illustrates a method for preventing insurance fraud in accordance with an embodiment of the present disclosure.

FIG. 8 illustrates a method for preventing opening of fraudulent accounts in accordance with an embodiment of the present disclosure.

Figure 9:
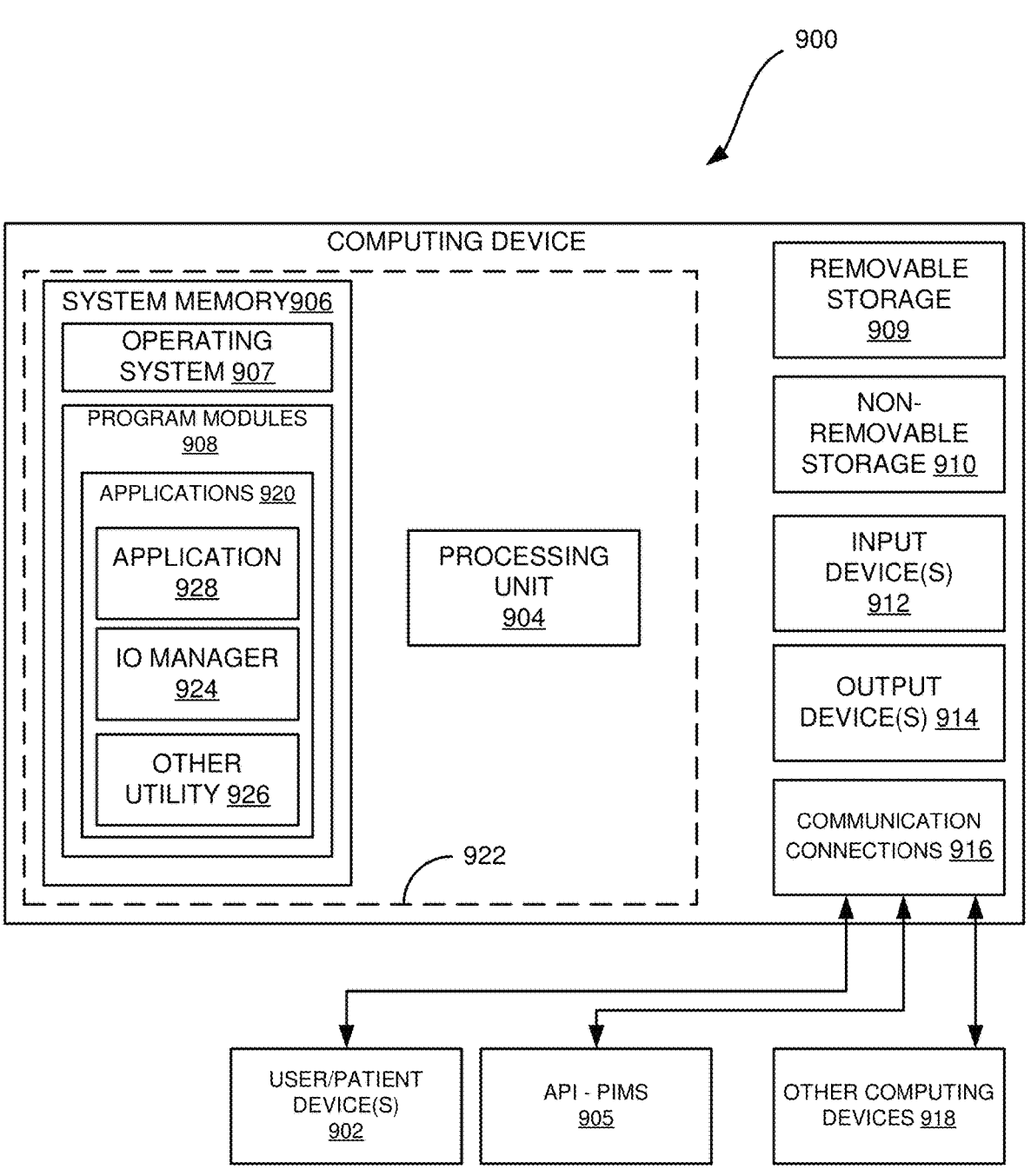

FIG. 9 is a block diagram of an exemplary computing device in accordance with an embodiment of the present disclosure It should be understood that the drawings are for purposes of illustrating the concepts of the disclosure and are not necessarily the only possible configuration for illustrating the disclosure.

DETAILED DESCRIPTION OF ILLUSTRATIVE EMBODIMENTS

The phrase "in one embodiment" is used repeatedly. The phrase generally does not refer to the same embodiment, however, it may. The terms "comprising", "having" and "including" are synonymous, unless the context dictates otherwise. The word "patient" is applicable in relation to the healthcare industry, whereas word "personal" is applicable in other industries alike, instead of the word "patient".

The patient's unique identity entity consists of two independent identification data objects such as patient's ID tag (PIT) formed from person individual data and a biometric data. Embodiments of the invention are discussed below with reference to the Figures. However, those skilled in the art will readily appreciate that the detailed description given herein with respect to these figures is for explanatory purposes as the invention extends beyond these limited embodiments.

For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. In addition, singular words should be read as plural and vice versa and masculine as feminine and vice versa, where appropriate, and alternative embodiments do not necessarily imply that the two are mutually exclusive. Identity Management In line with the current specification, a PIT is a specific string number which is formed by converting the person's full name, birthday and eye color by special following algorithm: the person's full name is the set of names by which an individual is known and that can be introduced as a word-group, with the understanding that, taken together, they all relate to that one individual. The full name must be presented from first/given, middle, and last/family/surname and mother's first name.

The first part of the patient's PIT number is formed from the length value of the full name string plus first character's coefficient number. For example: From the full name string removed all non-alphanumeric characters; The full name string value converted to uppercase; The first character's coefficient number is calculated as the sum of the ASCII values of the first letters of each word in the full name string. Additionally, the first part of the PIT includes a number that is based on a biometric data coefficient that is predetermined based on the bio characteristic of the patient. For example, if the biometric data is eye color, the eye color code will be based on eye color chart, potentially as follows: [0109] BLK Black=1 [0110] BLU Blue=2 [0111] BRO Brown=3 [0112] GRY Gray=4 [0113] GRN Green=5 [0114] HAZ Hazel=6

10

[0115] MAR Maroon=7 [0116] PNK Pink=8 [0117] DIC Dichromatic=9 [0118] SPC Spectrum=10.

The second part of the PIT number consists of the sum of ASCII value of each character in a full name string;

The third part of patient's PIT number preferably consists of a string joined of values from the day number plus the month number and the year of the birthday.

Thus, for example, for the person with full name "James Bob Smith", with the mother's name Sarah, with a date of birth May 15, 1926 and grey eye color, the PIT will be: 1330649681926515, where:

133064—is the First part of the PIT number and is formed from the length value (=13) of the full name string (James Bob Smith) without spaces and joined first character's coefficient number (83(S)+(74(J)+66(B)+83(S)=306); and 4 to the eye color.

| Here: | Sarah | s(83) |
| | James | J(74) |
| | Bob | B(66) |
| | Smith | S(83) |

968—is the Second part of the patient's PIT number and consists of the sum of ASCII value of each character in the full name string;

1926515—is the Third part of PIT number and consists of a string of values from the day number plus the month number and the year of the birthday.

Among other biometric data, ear images may be used which may be acquired in a similar manner to face images, and a number of researchers have suggested that the human ear is unique enough to each individual to allow practical use as a biometric. For obtaining biometric data of a person's ear can be used a simple video or digital camera. Ear biometric system consists of ear detection and ear recognition modules or algorithms.

There are several algorithms for image digitizing of human ear. Most popular shape-finding algorithm called "image ray transform," which boasts 99.6 percent accuracy, according to a study presented at the IEEE Fourth International Conference on Biometrics Sep. 29, 2014. The outer ear may prove to be one of the most accurate and least intrusive ways to identify people.

We propose that the analysis of the curve of the ear's helix to be the most reliable anatomical structure (antihelix, tragus, antitragus, inter-tragic incisura, and the ear lobule) when both left and right ears were paired together. In this approach, rate of identification should be close to 100%.

Since the unique identification, i.e., the Unique Patient Identification Entity (UPIE), consists of two independent identification data objects the requirements to high accuracy can be reduced. This approach boosts performance and reduces costs of measuring.

Figure 1:
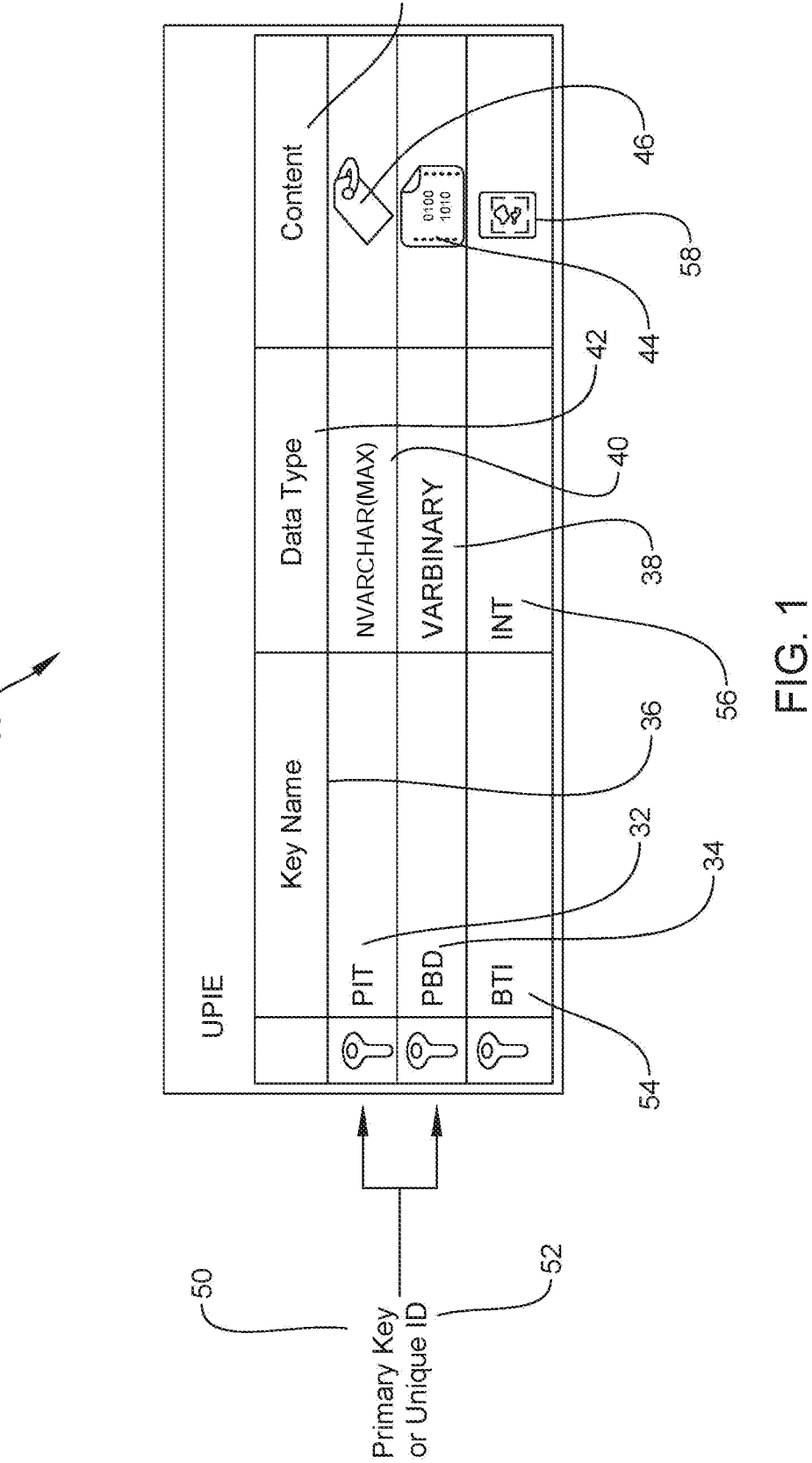
FIG. 1 illustrates the content and structure of Unique Patient Identity Entity.
Figure 2A:
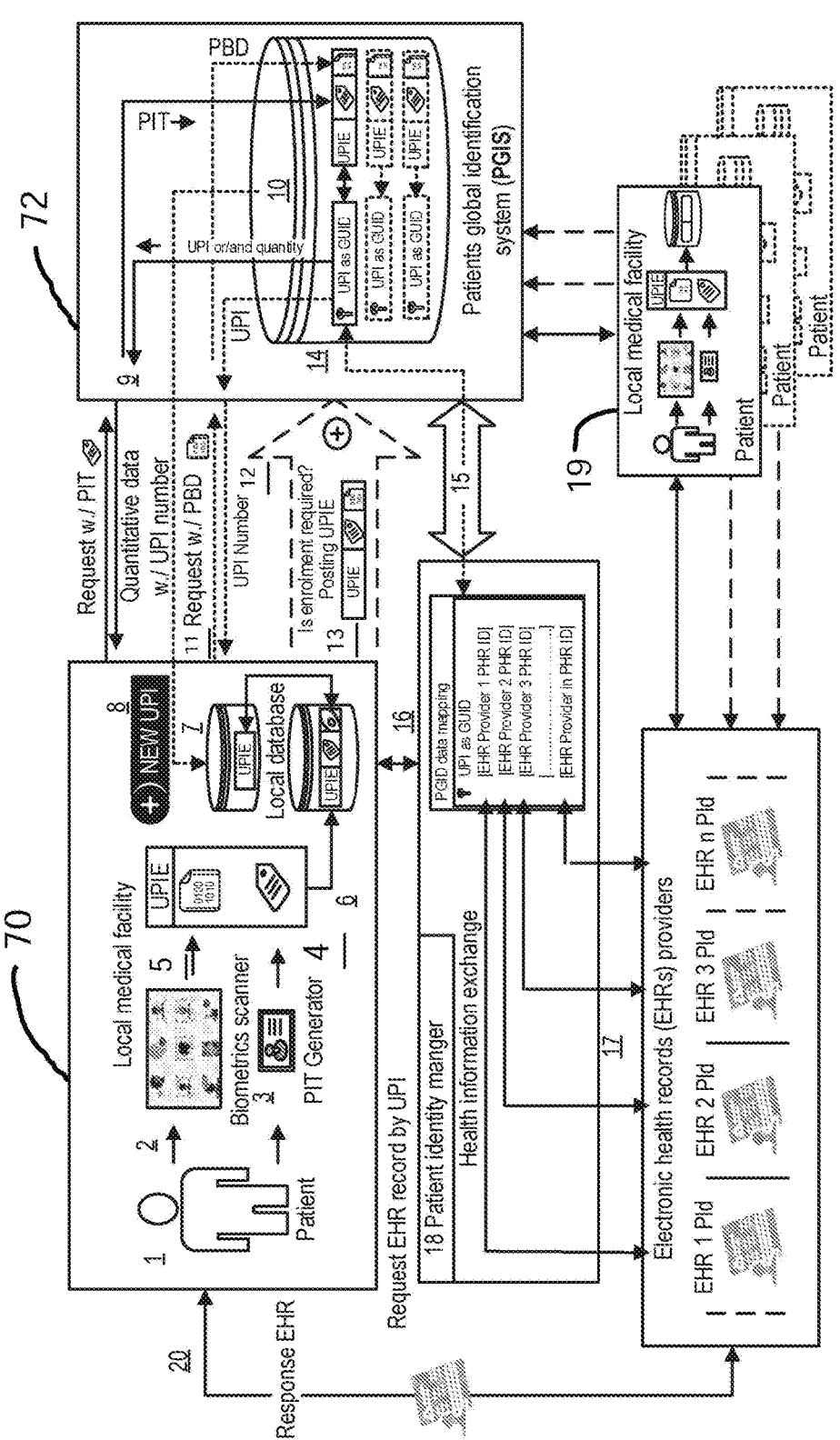
FIG. 2A illustrates a system and method of integrated patient, or person unique identity management, in accordance with one embodiment of the present invention.

Referring now to FIG. 1, as the example outlined for healthcare use, illustrated is the Unique Patient Identification Entity (UPIE) 30 having a PIT 32, as well as patient's biometric data (PBD) 34, where 44 is biometric data, e.g., digital data, that is used to uniquely identify each person. However, uniqueness is only guaranteed when the PIT 32 and PBD 34 are combined. This combination can be used in the nationwide Big Table (stored in the Patients global identification system (PGIS) as shown in FIG. 2) as a Primary Key (PK) 50 or unique ID 52 which consists from two rows PIT 32 and PBD 34. Each of their row is Candidate Key that can uniquely identify a patient's record in a Big Table. The PIT 32 row can be in string Data Type 42 with indexing that improves the speed of data retrieval operations to make select query run faster.

Shown are Data Type 42 including nvarchar (Max) 40, and varbinary 38 and INT 56. NVARCHAR (Max) 40 and VARBINARY 38 are SQL programming data storage types. Varbinary & Varbinary (max) are the binary string data types in SQL Server. These data types are used to store raw binary data up to a length of (32K–1) bytes. The contents of image files (BMP, TIFF, GIF, or JPEG format files), word files, text files, etc. are examples of binary data.

The Key Name column 36 includes PIT 32, PDB 34 and BTI 54. Content 48 has PIT 46, PBD 44, and string data Content 58. BTI 54 row is used to identify biometric input devices and their algorithms that can be standardized and unified for national use. INT 56 is Long Integer Content.

Because each single row's data can be duplicated but the combination values of these rows cannot be duplicated, the searching by string-based data in the first row of PIT 32 will reduce the amount of records for searching binary-based data in second row of PBD 34 data. The combination of PIT 32 and PBD 34 values called Unique Patient Identification Entity (UPIE) 30 and can be used in the various types of relational and non-relational databases.

The Unique Patient Identification Entity (UPIE) 30 comprises of both, PIT 32 and PBD 34 together, and forms a pair as Unique Identity Entity of person that uniquely identifies him among all other personal entities. Because value objects are immutable, it automatically fulfills the first requirement of identity: immutability. Because both values of objects, as a pair, are unique, they give it the second component of identity: uniqueness. Thereby, UPIE 30 is immutable and globally unique.

Referring now to FIG. 2, the figure illustrates Patients Global Unique Identification System (PGUIS) of the present invention. The uniqueness of this system architecture can be seen as simple cost-effective way to manage patients' identities across data sources, and the Unique Patient Identification Entity (UPIE) can be formed independently of the global system in any remote location, for example, on a server in a medical facility 70. The images of a person's (patient's) ears 1 are captured with a high-resolution camera and are stored in the files. The ear region of each image is located and extracted by the recognition system 2. On the next phase, the texture of the ear image is extracted 5 using linear time-invariant (LTI) filter responses and converts the texture to a virtual extraction feature (acquired bio-metric data) for right and left ears, respectively. Extraction features of both right and left ears paired together to the Patient Binary Biometric Data file (PBD).

Meanwhile, the program that calculates a PIT processes the patient's application data 4. When PIT and PBD objects are created they are combined in the unique patient (e.g., person, in case of industry other than medical) identification entity (UPIE) 6. The UPIE is stored in the local database 7 of a medical facility 10, sent to the global database 10 and saved in the global database 10 as UPI.
Patient Identity Management (PIM).

Electronic health care data are constantly being generated and linked across multiple systems, including electronic health records (EHRs), patient registries, and claims databases. In general, every system assigns its own identifier to each patient whose data it maintains. This makes it difficult to track patients across multiple systems and identify duplicate patients when different systems are linked. Efforts to address these challenges are complicated by the need to protect personal privacy and security.

Several standard development organizations are involved in the development of PIM strategies and standards. Major organizations currently include: Integrating the Healthcare Enterprise; Health Level Seven International; and The Regentrify Institute, Inc.

In accordance with the Patient Identity Management (PIM) system of the present invention, PGIS can be used as the foundational platform for a centralized countrywide level electronic database of all patients known as Central Data Repository (CDR) (containing all relevant data including biometrics in uniquely designed formats, all-time updated) for global level identity management.

Figure 3:
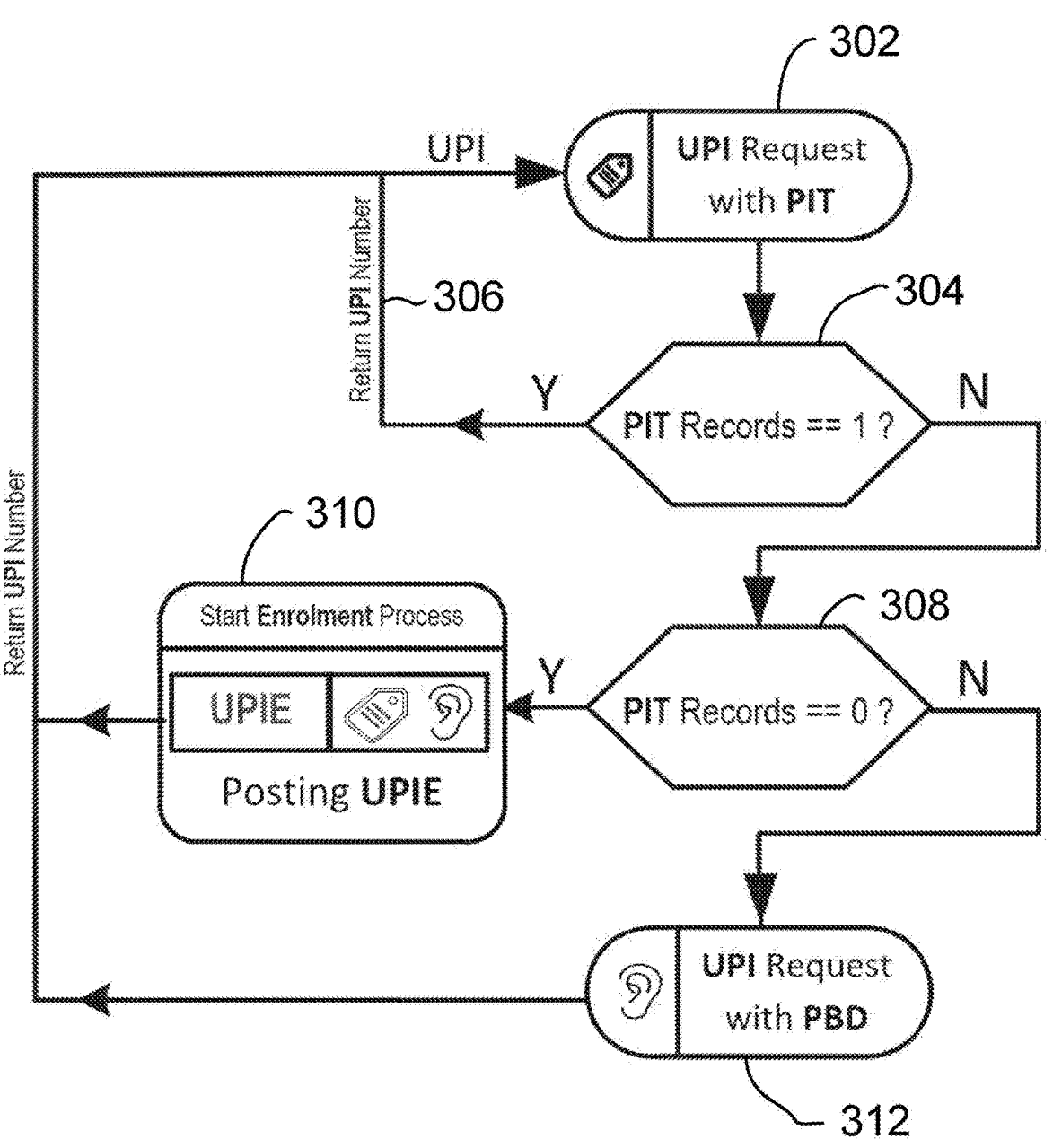
FIG. 3 illustrates a method of integrated patient, or person unique identity management, in accordance with one embodiment of the present invention.

To obtain a Unique Patient Identity (UPI) number from the global database 10 a special lightweight search algorithm is used as shown in FIG. 3 and described below.

The local medical facility application 70 sends PIT 8, see FIG. 2, to the patient global identification system PGIS 72 (e.g., a server or other computing device of the PGIS 72) as string number (9), in step 302. Because the PIT number itself can be unique, the PGIS response time to a request will be short. The PGIS fast response consists of small value of data (such as XML, JSON, or plain text) of two numbers: 1) total number of records in the PGIS Big Table in database 10 for requested PIT number, and 2) the GUID (Globally Unique ID) number of PIT record in the PGIS Big Table with the following variables: 1) if total number of records for requested PIT number equals to 1, or 2) to zero (null), or 3) if total number of records is more than 1. Depending on the value of the total number of records received from the PGIS Big Table for requested PIT number, the following processes are performed:

If total number of records in the PGIS Big Table for requested PIT number equals to 1, step 304, a server of the local medical facility 70 receives response 306 by UPI number 9. If total number of records in the PGIS Big Table for requested PIT number equals to zero, in step 308, the person's enrolment process is performed (step 310): local medical facility sends UPIE entity 13 to the PGIS and retrieves response by the same Global UPI (Unique Patient ((Person)) Identifier) number 9. If total number of records in the PGIS Big Table for requested PIT number equals to more than 1, the local medical facility sends request with PBD 11, in step 312, and receives the response by UPI number 12. In every case, the local medical facility may re-confirm if the PBD matches the PBD received from the PGIS BIG Table by scanning patient's PBD.

When the number of UPI have been obtained, local facility application updates UPIE record in local database 7 with UPI and utilizes UPI to make a request to EHR companies and providers 16 of electronic health records (EHR) by UPI.

As an example, Doctors in order for them to get patient's records, or send records must register themselves in the PGIS database 10 similarly while in their local medical facilities 70, registered doctors can delegate these duties to retrieve medical records to their auxiliaries, also.

Patient records can be obtained via the Patient Identity Manager 18. Doctor A in the local medical facility 70 after verification of patient UPI in the PGIS 72 either enrolls the patient, or proceed further to request the records.
Records Request.

Once the patient is identified as existing, the doctor with the permission of the patient enters patient's UPI into Patient Identity Manager 18 software interface, e.g., an API (application program interface) that interfaces with the server of the PGIS 72.

In the appropriate search box of Patent Identity Manager 18, the Doctor A types in verified patient's UPI, with patients authorization and clicks on search. After the search processes has been completed, the Doctor A is able to see the column of doctors EHR Providers 17 with the patient's records, past and current.

In that column, Doctor A checks which doctor's records he wants to obtain from the EHR Providers 17 and clicks on Submit Request button in the interface of Patient Identity Manager 18.

The EHR Providers 17, via a server or other computing device, receive requests with the UPI, identify the patient via UPI received from Doctor A, identify the records of the patient with this UPI, and respond within the allocated timeframe to Doctor A that the request has been received and the records are in process to be forwarded, and forward the records to Doctor A who was requesting the records from their local medical facility. The records may be shared via an internal temporary electronic encrypted file through a special repository.

On this proposed approach, the Patient Identity Management System (PIMS) is a part of the PDGUIS. The PIMS database contains records in which the Unique Patient Identifier (UPI) corresponds to the local identification number of patient health record on the provider's site. As shown in FIG. 2, Globally Unique ID or Global UPI is UPI saved in PGIS. Because it is located in the Global PGIS Server, it is for identification purpose called GUID, or UPI located in Global PGIS Server.

The electronic health care providers (17), i.e., servers of the various EHRs, see FIG. 2, make additional checkpoints for EHR using direct connection to the health information exchange system HIES (15). These are interchanges located between different hospital systems, local databases, governmental networks which have internal ID systems of their own. They do not belong to PGIS but patients are identified by UPI. The Health Information Exchange system (HIES) is intended to share electronic patient health (ePHI) records across disparate health care applications. This platform provides inter-mobility to exchange patient data produced by health care applications (19) with other applications that consume and use the data, such as EHRs, healthcare global ID verification for medical equipment, electronic record management and management of patient identity across data sources. A national patient identification system would identify patients, link medical records, and allow broad sharing, monitoring, research and analysis using computerized medical records linked through the nationwide health information network (NHIN).

Patient Global Unique Identification System (PGUIS)

The uniqueness of this system's architecture is allowing for a simple, cost-effective way to manage patient identity across data sources. In addition, the Unique Patient Identification Entity (UPIE) containing PIT and PBD data objects is formed independently of the global system in any remote location (i.e. medical facility). It is to be appreciated that all transactions, communications, etc. may be conducting by a processor, a server and/or a computing device disposed in the various locations, e.g., local medical facility 70, PGIS 72, Electronic health records (EHRs) providers 17, other local medical facilities 19. In certain embodiments, the transactions, communications, etc. between the processors, servers and/or computing devices will be conducted automatically with little or no human interaction.

The biometric information from an individual (1) is captured (2) and stored in the file/s as a binary patient biometric data file (PBD). It is to be appreciated that the biometric information may be obtained or captured by any suitable device, for example, a camera of a mobile device which may capture an image of at least one ear and then forward the image to a processor for further processing, e.g., feature extraction. Other biometric scanning devices may include, but are not limited to, a fingerprint scanner, an iris scanner, etc.

Preventing Pharmaceutical Fraud

One specific application of the inventive system and method is prevention of pharmaceutical fraud. Specifically, one way to obtain controlled substances from pharmacies is by using fake IDs. As an example, the NY Health Department's I-STOP/PMP—Internet System for Tracking Over-Prescribing—Prescription Monitoring Program Prescription Monitoring Program Registry, does not prevent distribution, or prescription filling of controlled substances prescribed via fraudulent picture IDs because it does not recognize the identities of the individuals on these IDs as fakes. As an example, some controlled substances are distributed in the USA to recovering drug users via the state sponsored programs. However, as described further below, non-drug users presenting different fake IDs to different medical providers can obtain such controlled substances for the purposes of reselling the drugs on the black market.

To control distribution, governmental agencies mandate that certain safeguards be maintained in the industry. For instance, under the current proposal, all prescriptions are written online since 2021 via a secured web base interface and a centralized server. However, despite this safeguard, fraudulent obtainment of personal identification data is highly probable, and there is a great chance that a prescription for controlled substances may be filled without proper monitoring and controlled substances be resold on the black market.

Some controlled substances (e.g., Suboxone) are supplied to people undergone through detoxification from drug addiction to prevent relapse via a very popular government funded program free of charge. Relapse rate after detoxification from the opioid abuse is estimated at 94%. This controlled substance prevents a relapse after the detoxification. Unfortunately, such relapses often result in overdose deaths because, at the time of relapse, relapsing addicts often take their last known to them dose without realizing that their tolerance to opioids became much lower during the detoxification. Typical cause of death due to opioid overdose is respiratory paralysis. For these individuals, the controlled medication which prevents the relapse is prescribed for life.

Unfortunately, depending on the quantity taken, the same medications can cause euphoric effects and can cause addiction on their own with a larger dose. Moreover, if the same medication is mixed with heroin, it potentiates the heroin effect.

Given today's prevalence of identity fraud and absence of reliable systems for people's identification, people who are not drug addicts but who know how to fake the urine test for opioids may still obtain these medications. Once the person tests positive for opioids, all that is needed for him/her to receive the controlled substance is to make a request to be placed into the program. As of this writing, once the fraudulent non-drug user is placed into the program, he/she will receive 30 tablets a month, one tablet for each day, every month for life to be available to sell on the black market. More tablets can be obtained if the fraudulent non-drug user uses several fake identities and fake IDs, registers using these IDs for the program from different medical providers, and then receives the drugs from different pharmacies. There is no way at present to identify these individuals and/or to detect them at the time when they obtain medications from pharmacies.

Nowadays, it is easier than ever to obtain fake IDs with the same picture, but with different first and last names and dates of birth, especially if information is mined and hacked. Because present biometric technologies are slow and are not 100% accurate, they are expensive to maintain and, therefore, they are underutilized. Further, a fake patient with a fake patient ID can get a prescription for an opioid in NY, fill it in NJ, and Department of Health in NY will not even know who obtained the medication. Even if they are interconnected at a later point, the medications are already dispensed and a fake individual is able to change his IDs number of times. A doctor's office or a pharmacy has no tools to authenticate the information from the IDs presented at the time when the patient presents at their location.

This is especially true if the pharmacy receives a valid doctor's prescription. All they have to do is validate the method of payment and make a copy of the presented picture ID. The I-STOP/PMP system at the time of prescription fill will recognize these fake individuals receiving their single monthly supply as legitimate individuals unrelated to each other and will not be able to detect the obtainment of the medications via fraudulent IDs. If there is no insurance information the pharmacy will be paid in cash, and the fraudulent individual will be free to re-sell the drugs on the black-market times more expensive.

In another aspect of the present invention, a method for preventing pharmaceutical fraud is provided using the above-described integrated identity management system. Specifically, the following steps are performed to prevent pharmaceutical fraud:

Patient (1) comes to see a doctor in a local medical facility and verification process is initiated. As shown in FIG. 2, the local medical facility sends out PIT to PGIS and receives one of the following:

Step 402, a server of the local medical facility receives data about a patient requesting a prescription to be filled, for example, by manual input of the data or scanning of a document with a patient's information;

Step 404, a processor or computing device encodes the received data as PIT;

Step 406, the processor at the local medical facility transmits the PIT to a computing device, e.g., a server, of a Patient Identity management System, (PIMS) to compare PIT to a plurality of PITs in a database;

Step 408, the processor of the local medical facility received a number of matches to the PIT;

Step 410, PIT Records equal to 0. If total number of records in the PGIS Big Table for requested PIT number equals to zero, the person enrolment process is performed in step 412: local medical facility sends UPIE entity (13) to the PGIS and receives response by UPI number (9).

Step 414, PIT Records equal to 1. If total number of records in the PGIS Big Table for requested PIT number equals to 1, the local medical facility receives response by UPI number (8). In step 416, biometric information of the patient is captured and converted into extraction features, in step 418. The features are compared to the biometric information associated to the PIT, in step 420, to determine if there is a match to confirm the patient's identity, in step 422.

Step 426, PIT Records equals to more than 1. If total number of records in the PGIS Big Table for requested PIT number is more than 1, step 426, the local medical facility sends request with PBD (11), in step 428 and receives the response by UPI number (12), step 430.

When the number of UPI have been obtained, the local facility application updates UPIE record in local database with (7) UPI and utilizes UPI to make a request to EHR companies and providers (16) of electronic health records (EHR) by UPI.

Once the patient's identity has been confirmed, the prescription is generated, in step 432, and the prescription is automatically transmitted to a predetermined pharmacy, in step 434, e.g., a server of the predetermined pharmacy.

Alternatively, in one embodiment, the server or computing device of the medical facility then sends the prescription and, associated with it, UPI first to a server or computing device of a controlling governmental body and waits for the response thereby creating the checkpoint at which the controlling body can very quickly electronically notify the medical facility of any identity conflict. If there is no identity conflict, the medical facility receives an automatic message to proceed by sending the electronic prescription to the pharmacy with the copy of the message that there are no identity conflicts.

Possible adverse outcomes: chances are that the governmental controlling body will receive too many requests under same UPI from different pharmacies within a very short time, or there will be a conflict of identity that will expose the fake patient.

Before the pharmacy fills the prescription, the pharmacist receives the verification (controlling body's message) and the data to make sure that the controlled substance and its UPI have no identity conflict. Once this is verified, the prescription can be filled.

When the above steps of the inventive method are followed, no controlled substance is filled before the receipt of a copy of the message that there is no identity conflict with the prescription medication and the associated UPI. An example of the identity conflict may be when the same prescription is written for the same UPI within an unusually short amount of time. If the medical facility receives the message that there is an identity conflict, the prescription is not generated, and, of course, not filled.

Identity Management for Finance Related Fraud

Identity management is equally important in finance related fraud. Some of the instances of finance related fraud are related to impersonating the owner of credit account (to whom the funds are payable) with amount of money is payable presenting his check to a paying account. In reality, the real owner of the paying account has no idea that his check is being manipulated in order to steal his funds. Other variations are possible. For example, commercial checks with large dollar amounts ($50,000 and more) are stolen and resold to interested criminal elements. Sometimes, the criminals also change the dollar amounts on the stolen checks.

Here is the flow of events: The criminals with stolen fake individual ID documents open a corporation with a similar to the payable entity's name in a different state and deposit the stolen check into the newly formed corporation for the purpose to cash the check and close the corporation. In this case, the owner of the check believes the payment was properly made and raises the issues with the bank only after the entity to whom the money should have been paid demands payment. The entity to whom the money should have been paid never receive payment, and the paying bank responds, when the claim is raised that the payment was properly processed because the account name was the same as identified on the check. Other frauds related to stealing money include Check Fraud, Account takeover, Phishing and Account opening fraud. All of the above can be linked and separated from each other in a chain of events and they can start from stealing the information written on the check. The checks are acquired from mail theft.

Finance related check fraud in US has an annual size of 250 billion dollar and is growing. Criminals steal mail keys and sell the keys on openly advertised Meta or telegram groups. Once there is a key obtained, usually all mailboxes in a particular zip code can be accessed to the criminals until the mailboxes are renewed with the new locks which by itself takes time. Their interest is obtainment of checks, and it does not matter the dollar amount on the check. The stolen checks will be sold anywhere from $50 to $250 each, depending on value of who the checks belong to. This usually happens in bigger city areas (Philadelphia metro area, NY City, etc.). Unemployment checks, cash checks are cashed only in the area where they were issued.

Also, there is valuable information on the check that the fraudsters can use to create a new check, or create a fake ID and open a fake bank account with a fake ID with the help of "Inies"—insiders who work within a bank, who secretly conspire with the criminals. Data on stolen checks can be used for other forms of frauds: fraudulent financial accounts, fraudulent loans, fraudulent IDs. It is used as a springboard for many more types of fraud.

Unfortunately, there is no regulation at this time that mandates regulation and provides systematic process on what financial institutions and related agencies have to do in an event of a stolen check and consequences arising out of the impact of this type of fraud. Finance related stolen check fraud claims processing time is usually manual and takes a lot of time. If there are two financial institutions fighting with each other in the claim, the result will be it is the customer who will be losing his money at the end. Legal challenges are equally complex and lengthy due to time it takes to complete necessary investigations and are by itself very labor-intensive, time involving and expensive proposition. Coordination with law enforcement and other investigative institutions that need to be involved with whom there may be no connection existing complicate the matters further. Many of the criminals masterminding the events are not even located in the US and remain out of the reach.

In order to prevent financial industry check fraud robust systems and methods must be implemented to protect client ID data to include a 3$^{rd}$ party verification system and communication to the real owner of the account of incoming debit for him to authorize it, or decline authorization in real time. The systems and methods of the present disclosure prevent financial stolen check fraud as will be described below in the following exemplary embodiments.

Preventing Check Fraud

Figure 5:
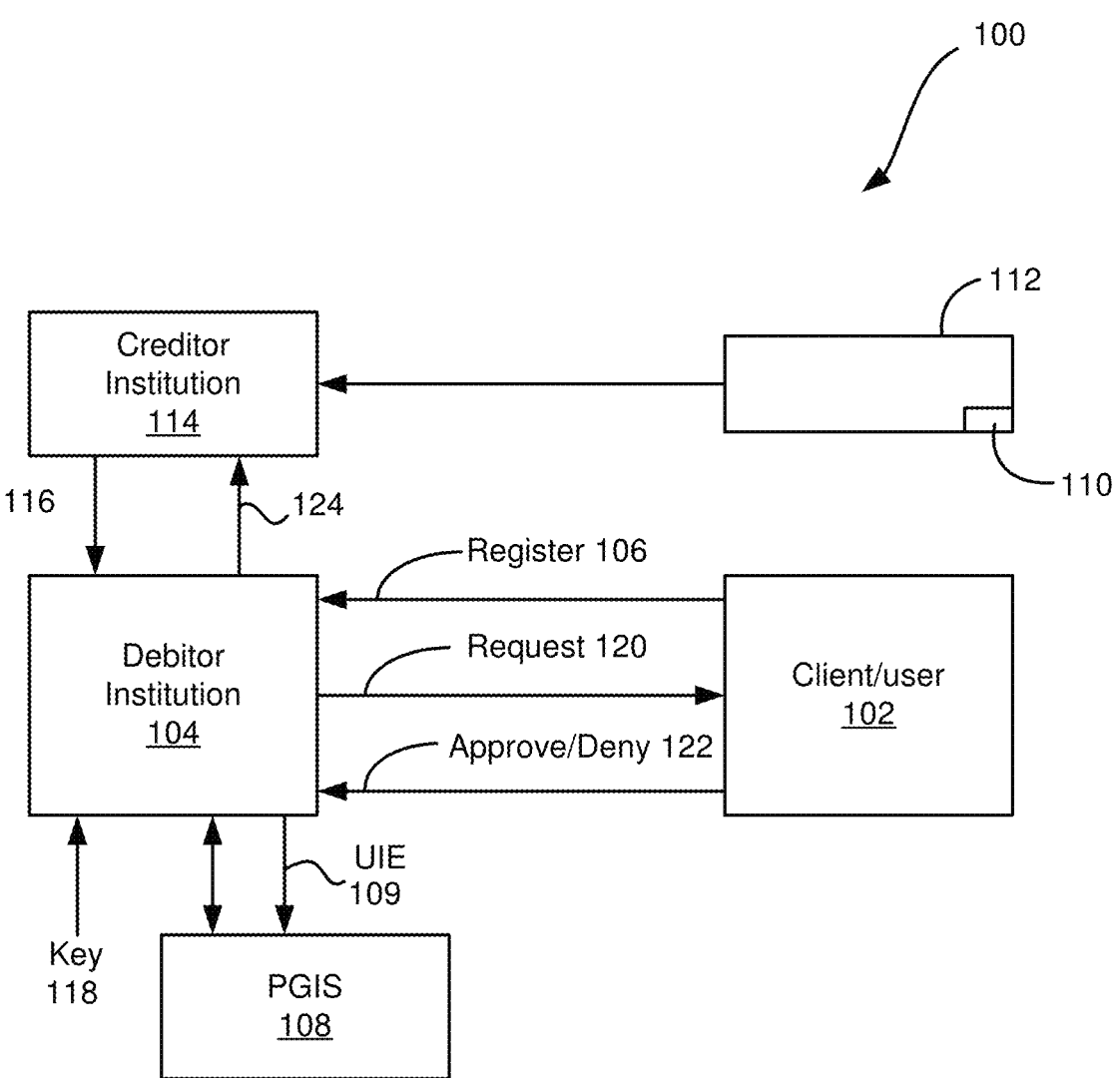
FIG. 5 illustrates a system and method for preventing check fraud in accordance with an embodiment of the present disclosure.

Referring to FIG. 5, a system 100 and method are provided for preventing check fraud. Initially, a Client/user 102, i.e., bank client, may register with his financial institution 104 where he will be assigned a UIE consisting of PIT and PBD. Client/user 102 sends a registration request 106 to a server or other computing device of the financial institution 104, where the registration request 106 includes identifying information necessary to create a PIT for the Client/user 102 (as described above). Additionally, the Client/user 102 may send biometric data (PBD) with the registration request 106. The biometric data may be captured by a mobile device of the Client/user 102, e.g., image of the user's ear, retinal scan, fingerprints, etc. The bank saves the user's PIT, PBD as, for example, face images and forms UIE 109 and sends it to PGIS 108 to form the UPI in the BIG Table, as described above.

PGIS 108 provides its API for banking institutions for them to transmit data and receive responses. The server/ computing device of the financial institution 104 then transmits the user's identifying information and biometric data to the PGIS 108, which creates a UPI for the user, as described above. The UPI is a digitized value encrypted as a barcode which can be decrypted only with a decryption key. The UPI barcode 110 is printed on the checks 112 of Client/user 102. The bank prints the UPI on each check with series numbers, for example:

1. UPI 9926449834/1, a barcode and check no 000001
2. UPI 9926449834/1, a barcode and check no 000002.
   :
   :
10. UPI 9926449834/1, a barcode and check no 000010

A Client/user 102, the payer or owner of a commercial bank account in the debtor banking institution 104 presented his check 112 to a third party to purchase an item, pay an invoice, etc. The third party then provides the check 112 to their financial institution 114, i.e., the creditor institution 114. The check may be presented by scanning the check and electronically transmitting the check to a server of their financial institution 114. Once the check 112 is scanned by the creditor institution 114, the creditor institution 114 sends the request for payment 116 to the debtor institution 104, e.g., to a server or other computing device, where the owner Client/user 102 of the payment check has his private, or his commercial account as an image of the check 112 on which there is a picture of the UPI code 110. As soon as the debit institution 104 gets the copy of the check 112, the UPI 110 on the check 112 gets decrypted with a decryption key 118 supplied by the PGIS 108. Based on the decrypted information, the debtor institution 104 may identify his Client/ user 102 and determine contact information of the Client/ user 102, e.g., an email address, a mobile phone number, etc. Referring to FIG. 5, an exemplary record for a user is illustrated. Based on the decrypted UPI 110, the user is identified and, in this example, a mobile number is identified. The debtor institution 104 may then send a request 120 to the Client/user 102 via his mobile number, to approve/ decline the payment/transaction of the check 112.

Figure 6:
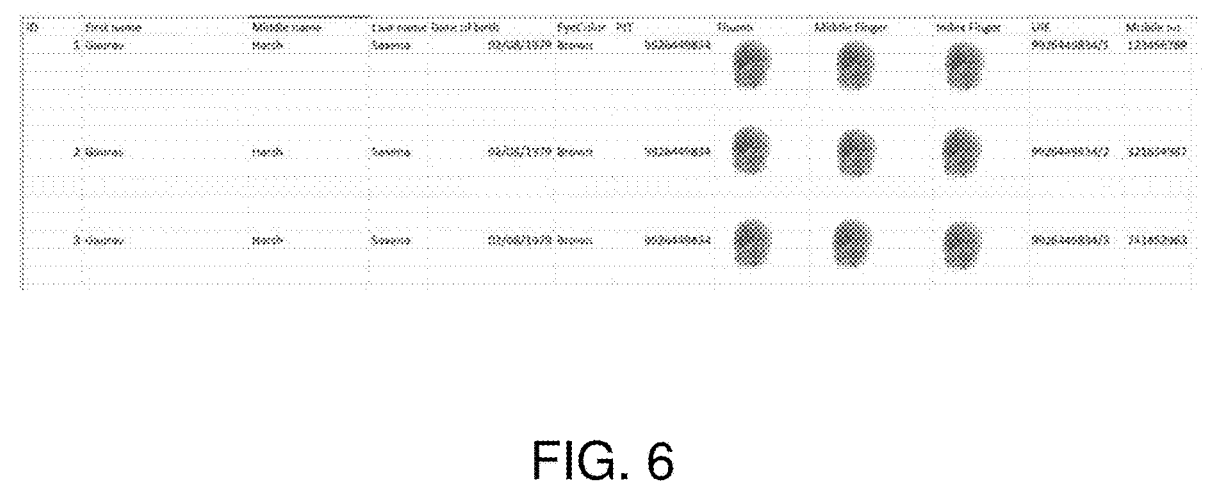

It is to be appreciated that the PBD may not only be one scan, different biometric items can be scanned, including a video stream of the face to include AI recognition in the UIE. In FIG. 6 what is shown is in use of 3 fingers scanned of the same individuals, as the PBD data for a particular UPI.

The debtor institution 104 employee entry scans of the bar code and the debit bank using PGIS software sends one notification to Client/user 102, for example:

Payee: Spinal Guides Labs
Address of the Payee: 97-77 Queens Blvd, 9$^{th}$ Floor
  Rego Park, NY 11374
Amount: 3,000.00$
In words: Three Thousand Dollars and Zero Cents
Date of check: Sep. 29, 2023
Check no: 000001

The Client/user 102 then logins into their account via a mobile app using the PBD that was used to create their account because in this chain of events we need to remove vulnerability of a mobile phone which can be hacked too. The Client/user 102 may approve or decline the transaction via the mobile app only after verifying his PBD. The approval/denial 122 is then transmitted to the server or other computing device of the debtor institution 104, or just a value change. If the Client/user 102 approved the transaction, a transmission 124 of funds are provided electronically to the creditor institution 114. If the Client/user 102 denied the transaction, a transmission 124 of a fraud alert is provided to the banking institutions 104 and 114.

For example, the Client/user 102 may receive a notification, via text, email, etc. When the Client/user 102 clicks on this notification, the Client/user 102 is automatically redirected to the mobile App of the PGIS (PGIS APP), where the Client/user 102 is asked to login. After successful login an Al Video app is opened and it gives the person random instruction for facial video imaging, for example, "turn your face to the left or turn your face to the right or turn your face Up or turn your face down", as a randomly directed process, as verification of the account owner's PBD. After the PGUIS system Al software (PBD part) finishes scanning, PBD matching with PIT concludes the UPI. In the event if there is no match, the person cannot authorize the payment.

It is to be appreciated that if PBD is not matched with the one that is with the UPI, the PGIS Mobile APP notifies to debit bank, as well, its client that "Someone is trying to access his account without authorization. Contact your banking institution." Alternatively, if the person or Client/user 102 is authenticated, the payment can be authorized. If the authenticated person, Client/user 102 sees a wrong amount requested to be paid, the authenticated person is able to cancel the payment, and put an alert on the account. In both of the cases PGIS App updates the status: if the authorized person clicks on "Ok" then Status is "OK" and the payment is authorized, and if he clicks on Cancel then the Status updated to "Cancel". If the debit bank client missed the notification to login sent via text or email then in the PGIS app of the debit bank computer software activates a voice call for the PGIS app to send a Robocall alert to the account owner, Client, to login. If then the account holder, Client/user 102, is not responding then the creditor institution 104 is notified by the debtor institution to the fact that the owner of the account is not accessible.

For loans applications, the individual's UPI has to be validated with the PGIS to make sure that this is the authentic individual who is applying for a loan.

Hacking of financial accounts with the PIT and PBD is impossible, as UPI will immediately identify a duplicate. It is impossible to have a third party to duplicate the system that has internal matching with binary data with use of Al life stream video. This is the best level in security. If a financial account is accessible just via a cell phone and a password, like most of the accounts today, the access is not secure as the SIM in the phone can be hacked, and when the password for the account is obtained via a cyber-hack the security of the account becomes breached.

For example, assume a person wants to open a fake bank account and brings all documents showing that he is the real person. The system after entering the person's information creates a PIT and sends the request to the Big Table to identify if there is an existence of the UPI with the same PIT. If it does not find the UPI then the enrollment is initiated and the PBD is entered, (with original government IDs) to substantiate that the person is the real one and UIE is sent to PGIS. The PGIS stores it as UPI sends back the UPI to the bank.

In this example, every person must register in PGIS (including bank employees). After the registration with the PGIS the UIE barcode is printed on all bank documents respective and belonging to this ID. A bank before opening the account for his client must always verify the individual.

Search under PIT does not have a requirement for high precision. If it comes back with value more than 1 it shows that the enrollment was done before to several PIT holders. All is required to locate the real person is to check the PBD.

It is possible to hack a mobile phone and get access into a banking app. However, when biometric live scanning video data sent to a third party for matching by Al software it is becoming simply impossible to breach the security of the account, and the inies (i.e., insiders) are useless to help. The same goes with a static PBD.

Possible scenarios to breach the PGIS security:

1. Stealing a barcode and placing it on the fake checks
   Not possible, because even if the barcode is possible to copy, and it gets decrypted the debit bank sends the message to the owner of the account, the Client, with request to review and authorize or decline the payment
2. Stealing PIT when applying for a loan
   Not possible because once there is existing PIT in the PGIS that means there should be PBD available, after matching of which the bank can verify if this is the real individual or not.
3. Stealing ID information and trying to open a fake bank account on a fake ID
   Not possible because once PIT request is sent to the PGIS, it will respond that this UPI is available and when the PBD verification is followed and the person is verified, and if this a fake individual the authorization to open an account will not be obtained. An "iny' who would need to receive this authorization to open a fake bank account for a fake customer will be unable to assist to open a bank account on a fake ID.
4. Stealing credentials to login into a mobile phone.
   Not possible because when the PBD is scanned it will be blocked in the event when the PBD will not match.

Preventing Insurance Fraud

In another embodiment, the systems and methods of the present disclosure verifies insurance payment release to patients for services done by non-participating providers. Initially, an UPI is formed for an insurance subscriber, i.e., a patient.

Each doctor under whom payments anticipated to be sent will be requested his UPI in the insurance company Database. Once the Insurance Company communicates UPI of the patient with PGIS, the doctors who saw the subscriber's UPI can be filtered, records can be requested by the insurance company from the doctor/s for verification.

The Insurance company filters the doctors who saw the subscriber's UPI and then requests records of subscriber's UPI from the doctor electronically via Patient Identity Manager 18. The insurance subscriber is the one who is the interested party, so the insurance company has to contact the medical facility within the PGIS for patient and procedure data verification.

Verification procedure (also can work for a participating provider):

1. All doctors and subscribers must be registered with PGIS
2. Insurance company sends the request to the PGIS for verification of identity of both, the doctor and the subscriber when the Insurance company received the request for payment.
3. PGIS sends the link to subscriber and the doctor to be verified for PBD
4. PBD verification must be completed to match in the UPI
5. Once they are verified the insurance company sends requests for records for the doctor and copy to his patient.

6. HIPAA compliant request for records will be send by the insurance to the doctor with the subscriber's UPI.

7. Once records represent the services performed and payment made by the patient, the insurance releases the payment check as patients' reimbursement to the patient Referring to FIG. 7, a method for preventing insurance fraud is provided. In step, 702, a server of an insurance company receives a request for payment from a patient. The request may include an invoice the patient received from the patient's doctor which forwarded electronically to the server of the insurance company, a wen generated form filled out by the patient, etc. In step 704, the server of the insurance company transmits a request for identity verification to the patient and the doctor associated to the patient, for example, by extracting the patient and doctor information from the request initiated in step 702. In step 706, a link is transmitted to the patient and doctor to verify their identities by their PBD, as described above. In step 708, if either the patient's PBD or the doctor's PBD does not match their respective UPIs, the server of the insurance company determines that the request for payment was fraudulent, step 710, and in one embodiment, will trigger an alert to the insurance company. If both the patient's PBD and the doctor's PBD does match their respective UPIs, in step 708, the identities are verified and the server of the insurance company transmits a request for the patient's record from the doctor, in step 712. In step 714, the server of the insurance company receives the patient's record and processes the records to determine if the patient's record is in accordance with a predetermined matching rules, in step 716. The records are reviewed and/or processed and if they are matching rules, the request for patient's reimbursement is allowed for his payment to non-participating with the patient's insurance provider and the requested payment is forwarded to the patient, in step 720. In one embodiment, upon approval in step 720, the payment is automatically forwarded to the patient electrically. In another embodiment, a check for the payment made be printed upon approval in step 720 for subsequent mailing to the patient. If the records do not match the predefined rules in step 716, the request for payment is denied, in step 718.

Preventing Opening of Fake Bank Accounts

Opening of fake bank accounts can only be done with fake IDs and inies (insiders in the banking institution). Fake bank accounts can be opened with the proof of mailing where a fake person would send a paper mail envelope to his address himself and present the stamped by the post office envelope to the banking institution as a prove of mailing.

This is how it is done: A fake person obtains an address and sends a post-stamped envelope via USPS mail currier to his address himself to match the address appeared as in the fake ID document. Once the USPS delivers the envelope, he presents the stamped unopened envelope to his bank to show the envelope processed by US Post Office. To add points, the fake person can order an internet service with the stolen data and fake ID. If the banking institution checks PIT and PBD the fake person is identified.

Additionally, the systems and methods of the present disclosure may be employed when withdrawing or cashing money from an ATM, where the transaction may only be completed with the PIT (1) and PBD (2) verification.

Referring to FIG. 8, a method of preventing opening of fraudulent bank accounts is provided. In step 802, a processor or server of a financial institution receives a request to open a new bank account. In step 804, the processor or computing device encodes the received data a PIT and, in step 806, the processor at the financial institution transmits the PIT to a computing device, e.g., a server, of a Person Identity management System, (PIMS) to compare PIT to a plurality of PITs in a database. In step 808, the processor of the financial institution receives a number of matches to the PIT. In step 810, PIT Records equal to 0. If total number of records in the PGIS Big Table for requested PIT number equals to zero, the person enrollment process is performed in step 812, as described above. When the number equals zero, it is an indication that the person does not exist in the PGIS Database.

Step 814, PIT Records equal to 1. If total number of records in the PGIS Big Table for requested PIT number equals to 1, the financial institution receives response by UPI number (9). In step 816, biometric information of the person is captured and converted into extraction features, in step 818. The features are compared to the biometric information associated to the PIT, in step 820, to determine if there is a match to confirm the patient's identity, in step 822. If there is no match, the person's identity is not verified, step 824.

Step 826 PIT Records equals to more than 1. If total number of records in the PGIS Big Table for requested PIT number is more than 1, step 826, the server of the financial institution sends request with PBD (11), in step 828 and receives the response by UPI number (12), step 830. In step 832, the UPI is compared to PBD presented by the user. If the identification with PBD does not match the returned UPI, the processor or server of the financial institution denies the opening of a new bank account.

FIG. 9 is a block diagram illustrating physical components of an exemplary computing device 900, for example, a client-computing device, a server, or any other computing device, with which examples of the present disclosure may be practiced. It is to be appreciated that computing device may include, but is not limited to, a server running the PIMS 18 at a local medical facility, a server at a financial institution, a server of the PGIS 70, a user device used to capture and/or verify a person's personal biometric data, etc. It is further to be appreciated that a server and/or other computing device mentioned above may be configured as a computing device 900 shown in FIG. 9 and described below.

In a basic configuration, the computing device 900 may include at least one processing unit 904 and a system memory 906. Depending on the configuration and type of computing device, the system memory 906 may comprise, but is not limited to, volatile storage (e.g., random access memory), non-volatile storage (e.g., read-only memory), flash memory, or any combination of such memories. The system memory 906 may include an operating system 907 and one or more program modules 908 suitable for running software programs/modules 920 such as IO manager 924, other utility 926 and application 928. As examples, system memory 906 may store instructions for execution. Other examples of system memory 906 may store data associated with applications. The operating system 907, for example, may be suitable for controlling the operation of the computing device 900. Furthermore, examples of the present disclosure may be practiced in conjunction with a graphics library, other operating systems, or any other application program and is not limited to any particular application or system. This basic configuration is illustrated in FIG. 9 by those components within a dashed line 922. The computing device 900 may have additional features or functionality. For example, the computing device 900 may also include additional data storage devices (removable and/or non-removable) such as, for example, magnetic disks, optical disks, or tape. Such additional storage is illustrated in FIG. 9 by a removable storage device 909 and a non-removable storage device 910.

As stated above, a number of program modules and data files may be stored in the system memory 906. While executing on the processing unit 904, program modules 908 (e.g., Input/Output (I/O) manager 924, other utility 926 and application 928) may perform processes including, but not limited to, one or more of the stages of the operations described throughout this disclosure. For example, one such application 928 may implement the API running on the PIMS at a local medical facility or financial institution. Other program modules that may be used in accordance with examples of the present disclosure may include electronic mail and contacts applications, word processing applications, spreadsheet applications, database applications, slide presentation applications, drawing or computer-aided application programs, photo editing applications, authoring applications, etc. It is to be appreciated that several modules or applications 928 may be execute simultaneously or near simultaneously and may share data.

Furthermore, examples of the present disclosure may be practiced in an electrical circuit comprising discrete electronic elements, packaged or integrated electronic chips containing logic gates, a circuit utilizing a microprocessor, or on a single chip containing electronic elements or microprocessors. For example, examples of the present disclosure may be practiced via a system-on-a-chip (SOC) where each or many of the components illustrated in FIG. 9 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality described herein may be operated via application-specific logic integrated with other components of the computing device 1106 on the single integrated circuit (chip). Examples of the present disclosure may also be practiced using other technologies capable of performing logical operations such as, for example, AND, OR, and NOT, including but not limited to mechanical, optical, fluidic, and quantum technologies. In addition, examples of the present disclosure may be practiced within a general purpose computer or in any other circuits or systems.

The computing device 900 may also have one or more input device(s) 912 such as a keyboard, a mouse, a pen, a sound input device, a device for voice input/recognition, a touch input device, etc. The output device(s) 914 such as a display, speakers, a printer, etc. may also be included. The aforementioned devices are examples and others may be used. The computing device 900 may include one or more communication connections 916 allowing communications with other computing devices 918 (e.g., external servers) and/or other devices of the system such as user/patient device 902, and/or computing device hosting PIMS 905. Examples of suitable communication connections 916 include, but are not limited to, a network interface card; RF transmitter, receiver, and/or transceiver circuitry; universal serial bus (USB), parallel, and/or serial ports; and/or wireless transceiver operating in accordance with, but not limited to, WIFI protocol, Bluetooth protocol, mesh-enabled protocol, etc.

The term computer readable media as used herein may include computer storage media. Computer storage media may include volatile and nonvolatile, removable and non-removable media implemented in any method or technology for storage of information, such as computer readable instructions, data structures, or program modules. The system memory 906, the removable storage device 909, and the non-removable storage device 910 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 902. Any such computer storage media may be part of the computing device 902. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

It is to be appreciated that the various features shown and described are interchangeable, that is a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. A computer-implemented method for retrieving a record of a patient comprising:

processing, by at least one processor, a set of personal data of a person to generate a specific integer number formed from said set of personal data by first converting a first type of personal data, wherein the first type of personal data comprises alphanumeric and non-alphanumeric characters, into a converted personal data string by removing all non-alphanumeric characters; next converting the converted personal data string to a second personal data string wherein all alphanumeric characters are in uppercase, then converting the second personal data string to a number string with at least four parts, wherein a first part is a number value which is calculated as the sum of ASCII values of first letters of each word in the converted personal data string, wherein a second part of said number string comprises values representing a selected day, wherein a third part of said number string is calculated from a length value of the words in the converted personal data string plus a coefficient number, wherein a fourth part of said number string is based on a physical characteristic of said person, and wherein said number string formed independently of a global computing system is used to identify said person;

processing, by the at least one processor, a set of biometric data formed independently of the global computing system obtained by scanning at least a portion of a body of said person with a biometric imaging device to obtain an image and then processing the image using at least one imaging algorithm to extract features of the portion of the body of said person;

combining, by the at least one processor, said generated number string with the extracted features of the portion of the body of said person to generate a unique person's identifier independently of the global computing system;

storing a plurality of unique person's identifiers in a database, each unique person's identifier having a respective generated number string and respective generated extracted features;

in response to a request for retrieval of at least one data record of a particular person, verifying, by the at least one processor, an identity of the particular person by comparing a received number string of said particular person to the number strings of the plurality of unique person's identifiers in the database and, if more than one match occurs, comparing said person's extracted features to the extracted features of the plurality of the matches of the unique person's identifiers to verify the identity of the particular person; and retrieving, by the at least one processor, at least one data record associated to the particular person upon verifying the identity of the particular person.

2. The computer implemented method of claim 1, wherein the portion of the body of said person is at least one ear of said person and the at least one imaging algorithm is an image ray transform function, wherein the image ray transform function locates and extracts at least one region of the ear.

3. The computer-implemented method of claim 1, wherein a portion of the first type of personal data is the full name of a person and a first name of a mother of said person.

4. The computer implemented method of claim 1, wherein the selected day is a birthday in a form of a combination of a day number, a month number, and a year number of the birthday.

5. The computer implemented method of claim 1, wherein a portion of the first type of personal data is a number representing an eye color of said person.

6. The personal data retrieval system of claim 1, wherein the at least one processor further processes an image of at least one of said person's palm vein, fingerprint, iris and face.

7. The computer implemented method of claim 1, wherein the at least one algorithm further converts the extracted regions of the ear into extracted features using linear time-invariant filter responses.

8. A system for generating a unique person identification entity (UPIE) formed locally independently of a global computing system comprising:

at least one processor that receives a set of personal data of a person and generates a personal identification tag (PIT) formed from said set of personal data by first converting a first type of personal data, wherein the first type of personal data comprises alphanumeric and non-alphanumeric characters, into a converted personal data string by removing all non-alphanumeric characters;

next converting the converted personal data string to a second personal data string wherein all alphanumeric characters are in uppercase, then converting the second personal data string to a number string with at least four parts, wherein a first part is a number value which is calculated as the sum of ASCII values of first letters of each word in the converted personal data string and on a physical characteristic of said person, wherein a second part of said number string comprises values representing a selected day, wherein a third part of said number string is calculated from a length value of the words in the converted personal data string plus a coefficient number; and a biometric scanning device coupled to the at least one processor, the biometric scanning device configured to capture a set of biometric data by scanning at least a portion of a body of said person to obtain an image and transmitting the obtained image to the at least one processor;

the at least one processor processes the obtained image using at least one imaging algorithm to extract features of the portion of the body of said person to create personal biometric data (PBD); and the at least one processor combines the personal identification tag (PIT) with personal biometric data (PBD) to generate a unique person identification entity (UPIE) and stores a plurality of unique person identification entities (UPIEs) in a database, each unique person identification entity (UPIE) having a respective generated personal identification tag (PIT) and respective generated personal biometric data (PBD), wherein the at least one processor verifies an identity of a particular person by comparing a received number string of the particular person to the personal identification tag (PIT) of the plurality of unique person identification entities (UPIEs) in the database and if more than one match occurs, comparing said person's personal biometric data (PBD) to the extracted features of the plurality of the matches of the unique person identification entities (UPIEs) to verify the identity of the particular person.

9. The system of claim 8, wherein the portion of the body of said person is at least one ear of said person and the at least one imaging algorithm is an image ray transform function, wherein the image ray transform function locates and extracts at least one region of the ear.

10. The system of claim 8, wherein a portion of the first type of personal data is the full name of a person and a first name of a mother of said person.

11. The system of claim 8, wherein the selected day is a birthday in a form of a combination of a day number, a month number, and a year number of the birthday.

12. The system of claim 8, wherein a portion of the first type of personal data is a number representing an eye color of said person.

13. The system of claim 8, wherein the at least one algorithm further converts the extracted regions of the ear into extracted features using linear time-invariant filter responses.

\* \* \* \* \*